(12) United States Patent
Pillarisetti et al.

(10) Patent No.: US 6,589,997 B2
(45) Date of Patent: Jul. 8, 2003

(54) SMALL-MOLECULE MODULATORS OF HEPATOCYTE GROWTH FACTOR/SCATTER FACTOR ACTIVITIES

(75) Inventors: Sivaram Pillarisetti, Norcross, GA (US); Itzhak D. Goldberg, Englewood, NJ (US)

(73) Assignee: North Shore-Long Island Jewish Health System, New Hyde Park, NY (US)

( * ) Notice: Subject to any disclaimer, the term of this patent is extended or adjusted under 35 U.S.C. 154(b) by 0 days.

(21) Appl. No.: 09/896,832

(22) Filed: Jun. 29, 2001

(65) Prior Publication Data

US 2003/0045559 A1 Mar. 6, 2003

(51) Int. Cl.$^7$ ................................. A01N 35/00
(52) U.S. Cl. ...................... 514/685; 514/277; 514/461; 514/438
(58) Field of Search ................. 514/685, 277, 514/401, 438

(56) References Cited

U.S. PATENT DOCUMENTS

| | | | | | |
|---|---|---|---|---|---|
| 4,219,569 | A | * | 8/1980 | Glenn | 514/685 |
| 4,279,930 | A | * | 7/1981 | Hall et al. | 514/546 |
| 4,439,418 | A | * | 3/1984 | Moller et al. | 424/73 |
| 6,346,550 | B2 | * | 2/2002 | Potter et al. | 514/685 |

* cited by examiner

*Primary Examiner*—James H. Reamer
(74) *Attorney, Agent, or Firm*—Klauber & Jackson

(57) ABSTRACT

The invention is directed to small organic molecules having the ability to mimic or agonize hepatocyte growth factor/scatter factor (HGF/SF) activity, or inhibit or antagonize HGF/SF activity, the former useful for promoting, for example, vascularization of tissues or organs for promoting wound or tissue healing, or augmenting or restoring blood flow to ischemic tissues such as the heart following myocardial infarction. Inhibition of cellular growth or proliferation is beneficial in the treatment, for example, of inflammatory diseases such as inflammatory joint and skin diseases, and dysproliferative diseases such as cancer.

5 Claims, 11 Drawing Sheets

Effect of met-3 compound (C6) on HUVEC proliferation

Specific effect of met-3 compound (C2) on SF mediated HUVEC proliferation

FIG. 6A
FIG. 6B
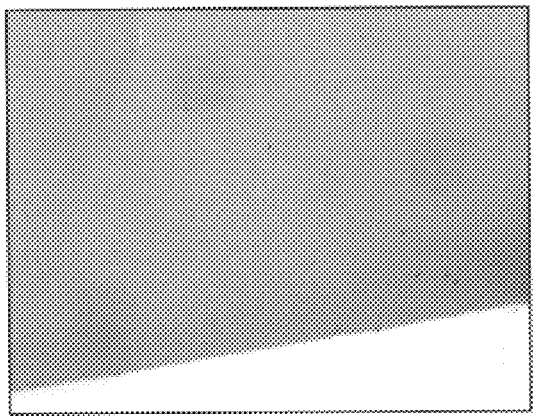
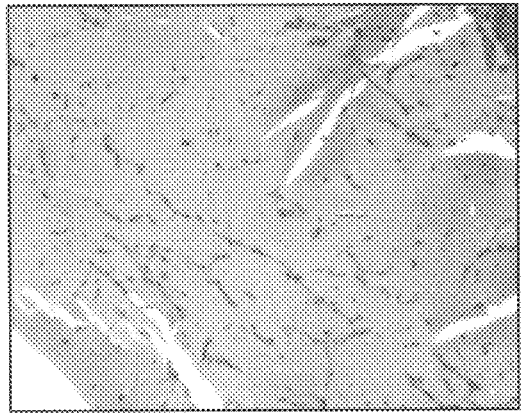

Effect of C-met-5 Analogue-M-8 on EC Proliferation

Effect of C-met-5 Analogue-M-8 on EC Proliferation

Effect of VEGF analogues on HUVEC proliferation

SMALL-MOLECULE MODULATORS OF HEPATOCYTE GROWTH FACTOR/SCATTER FACTOR ACTIVITIES

FIELD OF THE INVENTION

The invention is directed to various therapeutic uses of small molecule compounds having either hepatocyte growth factor/scatter factor (HGF/SF) activity, or the property of inhibiting the activity of HGF/SF. Such compounds have the potential for the treatment of conditions and diseases in which modulation of cellular proliferation, among other activities, is desired.

BACKGROUND OF THE INVENTION

Scatter factor (SF; also known as hepatocyte growth factor [HGF], and hereinafter referred to and abbreviated as HGF/SF) is a pleiotropic growth factor that stimulates cell growth, cell motility, morphogenesis and angiogenesis. HGF/SF is produced as an inactive monomer (~100 kDa) which is proteolytically converted to its active form. Active HGF/SF is a heparin-binding heterodimeric protein composed of a 62 kDa α chain and a 34 kDa β chain. HGF/SF is a potent mitogen for parenchymal liver, epithelial and endothelial cells (Matsumoto, K, and Nakamura, T., 1997, Hepatocyte growth factor (HGF) as a tissue organizer for organogenesis and regeneration. Biochem. Biophys. Res. Commun. 239, 639–44; Boros, P. and Miller, C. M., 1995, Hepatocyte growth factor: a multifunctional cytokine. Lancet 345, 293–5). It stimulates the growth of endothelial cells and also acts as a survival factor against endothelial cell death (Morishita, R, Nakamura, S, Nakamura, Y, Aoki, M, Moriguchi, A, Kida, I, Yo, Y, Matsumoto, K, Nakamura, T, Higaki, J, Ogihara, T, 1997, Potential role of an endothelium-specific growth factor, hepatocyte growth factor, on endothelial damage in diabetes. Diabetes 46:138–42). HGF/SF synthesized and secreted by vascular smooth muscle cells stimulate endothelial cells to proliferate, migrate and differentiate into capillary-like tubes in vitro (Grant, D. S, Kleinman, H. K., Goldberg, I. D., Bhargava, M. M., Nickoloff, B. J., Kinsella, J. L., Polverini, P., Rosen, E. M., 1993, Scatter factor induces blood vessel formation in vivo. Proc. Natl. Acad. Sci. U S A 90:1937–41; Morishita, R., Nakamura, S., Hayashi, S., Taniyama, Y., Moriguchi, A., Nagano, T., Taiji, M., Noguchi, H., Takeshita, S., Matsumoto, K., Nakamura, T., Higaki, J., Ogihara, T., 1999, Therapeutic angiogenesis induced by human recombinant hepatocyte growth factor in rabbit hind limb ischemia model as cytokine supplement therapy. Hypertension 33:1379–84). HGF/SF-containing implants in mouse subcutaneous tissue and rat cornea induce growth of new blood vessels from surrounding tissue. HGF/SF protein is expressed at sites of neovascularization including in tumors (Jeffers, M., Rong, S., Woude, G. F., 1996, Hepatocyte growth factor/scatter factor-Met signaling in tumorigenicity and invasion/metastasis. J. Mol. Med. 74:505–13; Moriyama, T., Kataoka, H., Koono, M., Wakisaka, S., 1999, Expression of hepatocyte growth factor/scatter factor and its receptor c-Met in brain tumors: evidence for a role in progression of astrocytic tumors Int. J. Mol. Med. 3:531–6). These findings suggest that HGF/SF plays a significant role in the formation and repair of blood vessels under physiologic and pathologic conditions. Further discussion of angiogenic proteins may be found in U.S. Pat. Nos. 6,011,009 and 5,997,868, both of which are incorporated herein by reference in their entireties.

Modulation of cellular proliferation by exogenously-supplied therapeutic agents has been offered as a new approach for the prophylaxis and/or treatment of various conditions and diseases in which limited cellular proliferation, or, in contrast, excessive proliferation of cells, is responsible for pathology, or at least for the prolongation of rebound from a pathological state to homeostasis. For example, the duration of wound healing, normalization of myocardial perfusion as a consequence of chronic cardiac ischemia or myocardial infarction, development or augmentation of collateral vessel development after vascular occlusion or to ischemic tissues or organs, and vascularization of grafted or transplanted tissues, organs, or wound healing, may be accelerated by promoting cellular proliferation, particularly of vascular cells.

In other cases where abnormal or excessive cellular proliferation is the cause of pathology, such as in dysproliferative diseases including cancer, inflammatory joint and skin diseases such as rheumatoid arthritis, and neovascularization in the eye as a consequence of diabetic retinopathy, suppression of cellular proliferation is a desired goal in the treatment of these and other conditions. In either case, therapy to promote or suppress proliferation may be beneficial locally but not systemically, and for a particular duration, and proliferation modulating therapies must be appropriately applied.

In co-pending application Ser. No. 09/606,628, filed Jun. 29, 2000, incorporated herein by reference in its entirety, peptide mimetics with HGF/SF-like, proliferative activity and particularly angiogenic activity, as well as other agents, particularly peptide HGF/SF antagonists which inhibit cellular proliferation and, in particular, angiogenesis, were described. Such peptides have uses, for example, in the treatment of inflammatory diseases, cancer, neovascularization, cardiac ischemia, wound healing, and other conditions in which modulation of cellular proliferation including blood vessel growth is therapeutically beneficial, as described above.

It is toward the identification of small organic molecules with HGF/SF activity, or those that inhibit HGF/SF activity, that the present invention is directed.

The citation of any reference herein should not be construed as an admission that such reference is available as "Prior Art" to the instant application.

SUMMARY OF THE INVENTION

In one broad aspect, the present invention is directed to methods for the modulation of hepatocyte growth factor/scatter factor (HGF/SF) activities in a mammal for the treatment of any of a number of conditions or diseases in which either HGF/SF has a therapeutically useful role, or in which the activity of endogenous HGF/SF is desirably inhibited or abrogated. Such modulation is achieved by the administration to the mammal of a compound of the invention in an amount effective to achieve the desired outcome. In one embodiment, the compounds of the invention modulate the activity of the HGF/SF receptor, c-Met. In a further embodiment, the compounds of the invention bind to c-Met.

In the instance where HGF/SF activity is desirable, certain compounds of the invention have been found to mimic or agonize the biological activities of HGF/SF, and thus are useful in the treatment, for example, of conditions or diseases in which enhanced cellular or vascular proliferation is desirable, among other desirable activities of HGF/SF. Such conditions or diseases include hepatic disease, renal disease, bone regeneration, hair growth, promoting wound or tissue healing, or augmenting or restoring blood flow to ischemic tissues such as the heart following myocardial infarction. Such compounds may be administered systemically or locally to particular tissues or organs, in order to achieve the desired systemic or local effect.

Such desirable activities also includes induction of proliferation of endothelial cells, induction of anti-apoptotic activity, induction of scatter activity, or any combination of the foregoing activities. In a preferred embodiment, any one of these activities is reduced or inhibited in the presence of exogenous c-Met receptor by a compound of the invention.

The compounds of the invention useful for mimicking or agonizing HGF/SF activity are characterized by being non-peptide, non-protein organic molecules with one or more of the activities of promoting proliferation of endothelial cells in vitro or in vivo, promoting angiogenesis in vitro or in vivo, increasing angiogenesis in wounds in vivo, promoting the growth of tumor cells in vitro or in vivo, promoting scatter, promoting anti-apoptotic activity, or inducing gene expression of angiogenic-cascade-related genes such as but not limited to IL-8 and angiopoietin-2. Preferred are compounds in which the aforementioned activity is inhibited or competed in the presence of exogenously-added c-Met receptor. The compounds may bind to c-Met. The present invention embraces the use of all such molecules for treatment of various conditions or diseases in which increased or enhanced HGF/SF activity is desirable. In one embodiment, the compounds of the invention have a molecular weight of under 1,000 Daltons, preferably above about 200 Daltons to about 1,000 Daltons; more preferably between about 300 Daltons and about 750 Daltons, and most preferably between about 300 Daltons and about 500 Daltons.

Thus, a method is provided for increasing hepatocyte growth factor/scatter factor (HGF/SF) activities in a mammal by administration to the mammal an effective amount of a compound having a molecular weight below 1,000 Daltons, the compound exhibiting HGF/SF-like activity in at least one of the following HGF/SF activity assays:

induction of proliferation of endothelial cells in vitro or in vivo;

induction of angiogenesis in vitro or in vivo;

increasing angiogenesis in wounds in vivo;

promoting tumor growth;

inducing gene expression of angiogenic-cascade-related genes such as but not limited to IL-8 and angiopoietin-2;

inducing anti-apoptotic activity; or inducing scatter activity.

In a preferred embodiment, the HGF/SF activity of the foregoing compound is inhibited in the presence of c-Met. In another preferred embodiment, the compounds bind to c-Met.

A compound of the invention may exhibits HGF/SF-like activity in at least two of the aforementioned HGF/SF activity assays, or in at least three of the HGF/SF activity assays, or in at least four said HGF/SF activity assays, or in at least five of the HGF/SF activity assays, or in at least six of the HGF/SF activity assays or in all of the HGF/SF activity assays. The compound preferably has a molecular weight between about 300 Daltons and about 750 Daltons, more preferably between about 300 Daltons and about 500 Daltons.

In another embodiment, the invention is directed to a method for the prophylaxis or treatment in a mammal of hepatic disease, renal disease, bone regeneration, hair growth, promoting wound or tissue healing, promoting vascularization of a tissue, promoting vascularization of an ischemic tissue, promoting vascularization of a tissue susceptible to ischemia, or augmenting or restoring blood flow to ischemic tissues such as the heart following myocardial infarction comprising administered systemically or locally to particular tissues or organ in need thereof an effective amount of a compound having a molecular weight between below about 1,000 Daltons, the compound exhibiting HGF/SF-like activity in at least one HGF/SF activity assays:

induction of proliferation of endothelial cells in vitro or in vivo;

induction of angiogenesis in vitro or in vivo;

increasing angiogenesis in wounds in vivo;

promoting tumor growth;

inducing gene expression of angiogenic-cascade-related genes such as but not limited to IL-8 and angiopoietin-2;

inducing anti-apoptotic activity; or inducing scatter activity.

In a preferred embodiment, the HGF/SF activity of the foregoing compound is inhibited in the presence of c-Met.

A compound of the invention may exhibits HGF/SF-like activity in at least two of the aforementioned HGF/SF activity assays, or in at least three of the HGF/SF activity assays, in at least five said HGF/SF assays, in at least six said HGF/SF assays, or in at least four said HGF/SF activity assays, or in all of the HGF/SF activity assays. The compound preferably has a molecular weight between about 200 Daltons and about 750 Daltons, more preferably between about 300 Daltons and about 500 Daltons.

The invention is also directed to a method for inhibiting the activity of hepatocyte growth factor/scatter factor (HGF/SF) in a mammal comprising administering to the mammal an effective amount of a compound having a molecular weight below about 1,000 Daltons, the compound exhibiting HGF/SF inhibitory or antagonistic activity in at least one of the following HGF/SF activity assays:

inhibiting proliferation of endothelial cells in vitro or in vivo;

inhibiting the growth of tumor cells in vitro or in vivo;

inhibiting scatter of normal or tumor cells; or inhibiting anti-apoptotic activity.

In a preferred embodiment, the HGF/SF inhibitory activity of the foregoing compound occurs in the presence of exogenously added HGF/SF or in cells or tissues in which HGF/SF is expressed or induced.

A compound of the invention may exhibit HGF/SF inhibitory activity in at least two of the aforementioned HGF/SF activity inhibition assays, or in at least three of the HGF/SF activity inhibition assays, or in all of the HGF/SF activity inhibition assays. The compound preferably has a molecular weight between about 200 Daltons and about 750 Daltons, more preferably between about 300 Daltons and about 500 Daltons.

In yet another embodiment, a method is provided for the prophylaxis or treatment in a mammal of a condition of disease selected from the group consisting of excessive cellular proliferation, angiogenesis, a dysproliferative disease, cancer, metastasis, inflammatory disease, diabetic retinopathy, inflammatory joint disease, and inflammatory skin disease comprising administering to a mammal an effective amount of a compound having a molecular weight below about 1,000 Daltons, said compound exhibiting HGF/SF inhibitory or antagonistic activity in at least one of the following HGF/SF activity inhibition assays:

inhibiting proliferation of endothelial cells in vitro or in vivo;

inhibiting the growth of tumor cells in vitro or in vivo;

inhibiting scatter of normal or tumor cells; and inhibiting anti-apoptotic activity.

In a preferred embodiment, the HGF/SF inhibitory activity of the foregoing compound occurs in the presence of exogenously added HGF/SF or in cells or tissues in which HGF/SF is expressed or induced.

A compound of the invention may exhibit HGF/SF inhibitory activity in at least two of the aforementioned HGF/SF activity inhibition assays, or in at least three of the HGF/SF activity inhibition assays, or in all of the HGF/SF activity inhibition assays. The compound preferably has a molecular weight between about 200 Daltons and about 750 Daltons, more preferably between about 300 Daltons and about 500 Daltons.

In another embodiment, the invention is directed to a method for the use for any of the aforementioned purposes of compounds that modulate HGF/SF activity with the general formula I:

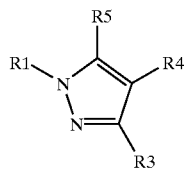

Formula I wherein
R3 and R5 are independently or together a straight-chain or branched C1–C6 alkyl optionally substituted with a cyano or halogen, halogen, trifluoromethyl or difluoromethyl groups;

R1 is hydrogen, methyl, CO-Aryl, $SO_2$-Aryl, CO-heteroaryl, or CO-alkyl; and R4 is $CH_2$-Aryl, halogen, arylcarbonylvinyl or S-heteroaryl.

Certain of the compounds of Formula I are novel, and the present invention is also directed to all such novel compounds with an activity as described herein.

The invention is also directed to a pharmaceutical composition comprising at least one compound of Formula I, in a pharmaceutically-acceptable carrier, for any of the uses described herein.

Non-limiting example of modulators of HGF/SF activity of Formula I include the following compounds, most of which, as will be seen in the examples below, exhibit HGF/SF agonist activity.

3-(5-chloro-1,3-dimethyl-1H-pyrazol-4-yl)-1-(4-chlorophenyl)prop-2-en-1-one [4-(2,6-dichlorobenzyl)-3, 5-dimethyl-1H-pyrazol-1-yl][3-(2,6-dichlorophenyl)-5-methylisoxazol-4-yl]methanone (4-(2-chloro-6-fluorobenzyl)-3,5-dimethyl-1H-pyrazole-1-yl)(3-(2,6-dichlorophenyl)-5-methylisoxazol-4-yl)methanone 4-(2-chloro-6-fluorobenzyl)-1-((3,4-dichlorophenyl)sulfonyl)-3,5-dimethyl1H-pyrazole 4-(2-chloro-6-fluorobenzyl)-1,3,5-trimethyl-1H-pyrazole 4-(2-chloro-6-fluorobenzyl)-3,5-dimethyl-1H-pyrazole (4-bromo-3,5-dimethyl-1H-pyrazol-1-yl)(3-(2,6-dichlorophenyl)isoxazole-4-carbohydrazide) 3-(4-(2,6-dichlorobenzyl)-3,5-dimethyl-1H-pyrazol-1-yl)propanenitrile 3,5-di(tert-butyl)-4-(2-chloro-6-fluorobenzyl)-1H-pyrazole (4-(2-chloro-6-fluorobenzyl)-3,5-dimethyl-1H-pyrazole-1-yl)(2,6-dichlorophenyl)methanone 1-(4-(2-chloro-6-fluorobenzyl)-3,5-dimethyl-1H-pyrazole-1-yl)2,2-dimethylpropan-1-one (4-(2-chloro-6-fluorobenzyl)-3,5-dimethyl-1H-pyrazole-1-yl)(4-chlorophenyl)methanone (4-(2-chloro-6-fluorobenzyl)-3,5-dimethyl-1H-pyrazole-1-yl)(2-thienyl)methanone (4-chlorophenyl)(3,5-dimethyl-4-((1-methyl-1H-imidazol-2-yl)thio)-1H-pyrazol-1-yl) methanone In another embodiment, the invention is directed to methods for the use for the aforementioned purposes of compounds that modulate HGF/SF activity with the general formula II:

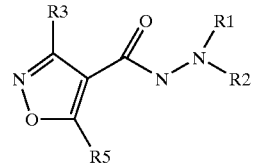

Formula II wherein
R5 is a C1 to C6 branched or straight-chained alkyl group;

R3 is a substituted or unsubstituted Aryl group;

R1 is hydrogen or a C1 to C4 straight-chained, branched or cycloalkyl group;

R2 is $COCH_2ONCH$-Aryl; heteroaryl, $COCH_2CH_2Aryl$; Aryl; COS-Aryl; CO-Heteroaryl; C1 to C4 straight-chained alkyl, branched alkyl, or cycloalkyl; or wherein R1 and R2 form a cyclic group of 5 or 6 carbon atoms.

Certain of the compounds of Formula II are novel, and the present invention is directed to all such novel compounds with an activity as described herein.

The invention is also directed to a pharmaceutical composition comprising at least one compound of Formula II, in a pharmaceutically-acceptable carrier, for any of the uses described herein.

Most of the compounds of Formula II exhibit HGF/SF antagonist or inhibitory activity, as will be seen in the examples below. Non-limiting examples of compounds of Formula II include N'4,5-dimethyl-N'4-(5-nitro-2-pyridyl)-3-(2,6-dichlorophenyl)isoxazole-4-carbohydrazide N'4-(2-(((2, 4-dichlorobenzylidene)amino)oxy)acetyl)-3-(2,6-dichlorophenyl)-5-methylisoxazole-4-carbohydrazide N'4-(3-(3,4,5-trimethoxyphenyl)propanoyl)-3-(2,6-dichlorophenyl)-5-methylisoxazole-4-carbohydrazide 2-nitrophenyl 2-((3-(2,6-dichlorophenyl)-5-methylisoxazol-4-yl)carbonyl)hydrazine-1-carbothioate N'4-((2-methyl-1,3-thiazol-4-4yl)carbonyl)-3-(2,6-dichlorophenyl)-5-methylisoxazole-4-4carbohydrazide N1-((2-((3-(2,6-dichlorophenyl)-5-methylisoxazol-4-yl)carbonyl)hydrazino)(methylthio)methylidene)benzene-1-sulfonamide N'4-(2,4,6-trichlorophenyl)-3-3(2,6-dichlorophenyl)-5-methylisoxazole-4-carbohydrazide N'4,3-di(2,6-dichlorophenyl)-5-methylisoxazole-4-carbohydrazide N'4-(3,5-dichloro-4-pyridyl)-3-(2,6-dichlorophenyl)-5-methylisoxazole-4-carbohydrazide N'4-phenyl-3-(2,6-dichlorophenyl)-5-methylisoxazole-4-carbohydrazide N'4, N'4,5-trimethyl-3-(2,6-dichlorophenyl)isoxazole-4-carbohydrazide N4-azepan-1-yl-3-(2,6-dichlorophenyl)-5-methylisoxazole-4-carboxamide N'4-(6-(trifluoromethyl)-2-pyridyl)-3-(2,6-dichlorophenyl)-5-methylisoxazole-4-carbohydrazide N'4-(3,3-diethoxypropanoyl)-3-(2,6-dichlorophenyl)-5-methylisoxazole-4-carbohydrazide In a further embodiment, the invention is directed to methods for the use for any of the aforementioned purposes of compounds that modulate HGF/SF activity with the general formula III:

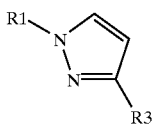

Formula III wherein

R1 is SO$_2$Alkyl, SO$_2$-Aryl, CO-t-Butyl, COAryl, CON-HAlkyl; CONHAryl; and

R3 is CHCH-heteroaryl; phenoxyphenyl; heteroaryl; or Aryl substituted heteroaryl.

Certain of the compounds of Formula III are novel, and the present invention is directed to all such novel compounds with an activity as described herein.

The invention is also directed to a pharmaceutical composition comprising at least one compound of Formula III, in a pharmaceutically-acceptable carrier, for any of the uses described herein.

These compounds generally exhibit HGF/SF stimulatory or agonist activity. Non-limiting examples of compounds of Formula III include (4-chlorophenyl)[3-(2-(2-thienyl)vinyl)-1H-pyrazol-1-yl] methanone; 1-(methylsulfonyl)-3-(2-(2-thienyl)vinyl)-1H-pyrazole; 2,2-dimethyl-1-(3-(2-(2-thienyl)vinyl)-1H-pyrazole1-yl)propan1-one N-methyl-3-(2-(2-thienyl) vinyl)-1H-pyrazole-1-carboxamide (4-chlorophenyl)(3-(3-phenylisoxazol-5-yl)-1H-pyrazol-1-yl)methanone (4-chlorophenyl)(3-(3-(4-chlorophenyl)-5-methylisoxazol-4-yl)-1H-pyrazol-1-yl)methanone (4-chlorophenyl)(3-(5-(2-thienyl)-2-thienyl)-1H-pyrazol1-yl)methanone (2,4-dichlorophenyl)(3-(5-(2,4-difluorophenyl)-2-furyl)-1H-pyrazol-1-yl)methanone N1-phenyl-3-(2-(2-thienyl)vinyl)-1H-pyrazole-1-carboxamide (4-chlorophenyl)(3-(2-(5-(2-thienyl)-2-thienyl)-4-methyl-1,3-thiazol-5-yl)-1H-pyrazol-1-yl) methanone (3-benzhydryl-1H-pyrazol-1-yl)(4-chlorophenyl)methanone N1-(4-chlorophenyl)-3-(2-(2-thienyl)vinyl)-1H-pyrazole-1-carboxamide (4-chlorophenyl)(3-(2-methylimidazo(1,2-a)pyridin-3-yl)-1H-pyrazol-1-yl)methanone 2-chloro-6-(4-(1-(4-chlorobenzyl)-1H-pyrazol-3-yl)phenoxy)benzonitrile 1-((4-chlorophenyl)sulfonyl)-3-(2-(2-thienyl)vinyl)-1H-pyrazole In a further embodiment, the invention is directed to methods for the use for any of the aforementioned purposes of compounds that modulate HGF/SF activity with the general formula IV:

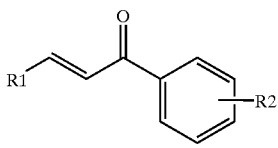

Formula IV

Wherein

R1 is Aryl or Heteroaryl; and

R2 is one or more halogen, nitro, C1 to C4 straight-chained alkyl, branched alkyl, or cycloalkyl, or C1 to C4 alkyloxy groups.

Certain of the compounds of Formula IV are novel, and the present invention is directed to all such novel compounds with an activity as described herein.

The invention is also directed to a pharmaceutical composition comprising at least one compound of Formula IV, in a pharmaceutically-acceptable carrier, for any of the uses described herein.

The compounds in this group may be HGF/SF agonists or antagonists. Non-limiting examples of modulators of Formula IV include:

1-(4-chloro-3-methylphenyl)-3-(2,6-dichlorophenyl)-prop-2-en-1-one 1-(4-chloro-3-methylphenyl)-3-(2-chlorophenyl)prop-2-en-1-one 3-(2-chloro-6-fluorophenyl)-1-(4-chloro-3-methylphenyl)prop-2-en-1-one 3-(4-bromo-2-thienyl)-1-(3,4-dichlorophenyl)prop-2-en-1-one 3-(4-bromo-2-thienyl)-1-(4-chloro-3-methylphenyl)prop-2-en-1-one 3-(4-bromo-2-thienyl)-1-(4-fluorophenyl)prop-2-en-1-one 3-(4-bromo-2-thienyl)-1-(4-chlorophenyl)prop-2-en-1-one 1-(4-chlorophenyl)-3-(2,4-dichlorophenyl)prop-2-en-1-one 3-(1,3-benzodioxol-5-yl)-1-(4-bromophenyl)prop-2-en-1-one 3-(3-phenoxy-2-thienyl)-1-(2-thienyl)prop-2-en-1-one 3-(3-bromo-4-methoxyphenyl)-1-phenylprop-2-en-one 3-(3,4-dichlorophenyl)-1-(2-nitrophenyl)prop-2-en-1-one 1-(4-chlorophenyl)-3-(3,4-dichlorophenyl)prop-2-en-1-one 1-(4-chlorophenyl)-3-(3,5-dichloro-2-hydroxyphenyl)prop-2-en-1-one 1-(2-chlorophenyl)-3-(3,5-dichloro-2-hydroxyphenyl)prop-2-en-1-one 3-(4-chlorophenyl)-1-(2,6-dichlorophenyl)prop-2-en-1-one 1-(4-bromophenyl)-3-(4-chlorophenyl)prop-2-en-1-one 1-(2-chlorophenyl)-3-(2,6-dichlorophenyl)prop-2-en-1-one 1-(4-chlorophenyl)-3-(2,6-dichlorophenyl)prop-2-en-1-one 3-(2,6-dichlorophenyl)-1-(4-methoxyphenyl)prop-2-en-1-one 3-(4-chloro1-methyl-1H-pyrazol-3-yl)-1-[4-(trifluoromethyl)phenyl]prop-2-en-1-one 3-(2,4-dichlorophenyl)-1-(2-methylphenyl)prop-2-en-1-one 3-(2,6-dichlorophenyl)-1-(2-methylphenyl)prop-2-en-1-one 3-(3,4-dichlorophenyl)-1-(2-methylphenyl)prop-2-en-1-one 3-(5-bromo-2-hydroxyphenyl)-1-(3-methylphenyl)prop-2-en-1-one 3-(5-bromo-2-hydroxyphenyl)-1-(4-methylphenyl)prop-2-en-1-one 3-(2,4-dichlorophenyl)-1-(3-methylphenyl)prop-2-en-1-one 3-(2,4-dichlorophenyl)-1-(4-methoxyphenyl)prop-2-en-1-one 1-[4-amino-2-(methylthio)-1,3-thiazol-5-yl]-3-(4-chlorophenyl)prop-2-en-1-one 1-(4-chlorophenyl)-3-[4-(trifluoromethyl)phenyl]prop-2-en-1-one 1-benzo[b]thiophen-3-yl-3-(4-chlorophenyl)prop-2-en-1-one 1,3-di(5-nitro-3-thienyl)prop-2-en-1-one 1-(4-bromophenyl)-3-(3,5-difluorophenyl)prop-2-en-1-one 3-(3,5-difluorophenyl)-1-(3-nitrophenyl)prop-2-en-1-one The foregoing general and specific structures of compounds with HGF/SF activity are merely illustrative of compounds of the invention with the desired activities, and are in no way limiting.

In a further embodiment, the invention is directed to pharmaceutical compositions comprising any one or a combination of the foregoing compounds, together with a pharmaceutically-acceptable carrier, for use in any of the aforementioned purposes.

In a further embodiment, the aforementioned compounds with activities of promotion of cellular proliferation or angiogenesis are useful for promoting vascularization of a tissue, particularly of an ischemic tissue or a tissue susceptible to ischemia.

Prophylaxis or treatment may be provided by contacting the tissue with an effective angiogenic amount of an agent of the invention. Contact may be provided by any appropriate means to deliver an effective amount of the agent for a duration to achieve the desired results. By way of non-limiting example, topical application may be applied to the desired target, or by infusion, bathing, or implantation of a sustained delivery device. For systemic administration, oral or parenteral routes may be employed. The target cells or tissue may be, for example, a transplanted or grafted tissue or organ such as skin, heart, vascular tissue or kidney, an ischemic organ, such as a heart following myocardial infarction or angina, a tissue or organ damaged by wounding, surgical intervention, vascular tissue, neural tissue, a wound, ulcer, etc. The cells may be, by way of non-limiting example, epithelial cells, endothelial cells, and smooth muscle cells, and tissues and organs comprising such cells. Promotion of growth and/or regeneration of neural tissue, teeth, and other tissues are embraced herein. Preferred cells, organs and tissues comprise the c-Met receptor.

The aforementioned compounds with HGF/SF activity are also desirably useful for the treatment of various hepatic diseases including cirrhosis and liver failure; various renal diseases including renal failure. The compounds are also useful for inducing bone regeneration.

In another broad aspect of the invention, undesirable activities of HGF/SF in vivo may be therapeutically inhibited by the administration to a mammal of an effective amount of certain compounds of the invention for the treatment of various conditions and diseases generally involved in cellular proliferation and angiogenesis, among others. Inhibition of HGF/SF is desired, for example, in the treatment of dysproliferative diseases such as cancer and metastases, as well as various inflammatory diseases such as inflammatory joint and skin diseases. Other activities include but are not limited to inhibition of endothelial cell proliferation, inhibition of angiogenesis, angiostasis, tumoricidal activity, and any combination of the foregoing. In a further embodiment, the agents inhibit activity in the presence of exogenously-added or in cells in which activity is present or induced. Abnormal vascular proliferation such as occurs in diabetic retinopathy is also treatable by the methods of the invention.

The compounds of the invention useful for inhibiting HGF/SF activity are characterized by being non-peptide, non-protein, organic molecules with one or more of the activities of inhibiting proliferation of endothelial cells in vitro or in vivo, inhibiting the growth, scatter or metastasis of tumor cells in vitro or in vivo, inhibiting scatter, or inhibiting anti-apoptotic activity. Preferred are compounds in which such activities are exhibitable in the presence of exogenously-added HGF/SF. The present invention embraces the use of all such molecules for treatment of various conditions or diseases in which decreased or inhibited HGF/SF activity is desirable.

In a further aspect, the invention is directed to pharmaceutical compositions comprising any one or a combination of any of the foregoing compounds, together with a pharmaceutically-acceptable carrier.

The aforementioned compounds are useful for the treatment of dysproliferative or angiogenic diseases, such as but not limited to a tumor or metastasis, or psoriasis, or a tissue or organ involved in inflammatory diseases such as rheumatoid arthritis, the eye involved in neovascularization such as results from chronic diabetes, an abnormal growth such as keloid formation during wound healing, or a desired intentional disruption of cellular proliferation such as to prevent the genesis or maturation of a developing organ or tissue. Methods of treatment include application of a compound of the invention to the desired target site(s), in the form of a pharmaceutical composition comprising one or more compounds of the invention.

The foregoing general and specific structures of compounds with HGF/SF inhibitory or antagonizing activity are merely illustrative of compounds of the invention with the desired activities, and are in no way limiting.

These and other aspects of the present invention will be better appreciated by reference to the following drawings and Detailed Description.

BRIEF DESCRIPTION OF THE DRAWINGS

FIGS. 6A–B shows the results from a Matrigel in-vivo assay using 1-(4-chloro-3-methylphenyl)-3-(2,6-dichlorophenyl)-prop-2-en-1-one and (4-(2-chloro-6-fluorobenzyl)-3,5-dimethyl-1H-pyrazole-1-yl)(3-(2,6-dichlorophenyl)-5-methylisoxazol-4-yl)methanone, respectively.

DETAILED DESCRIPTION OF THE INVENTION

Figure 1:
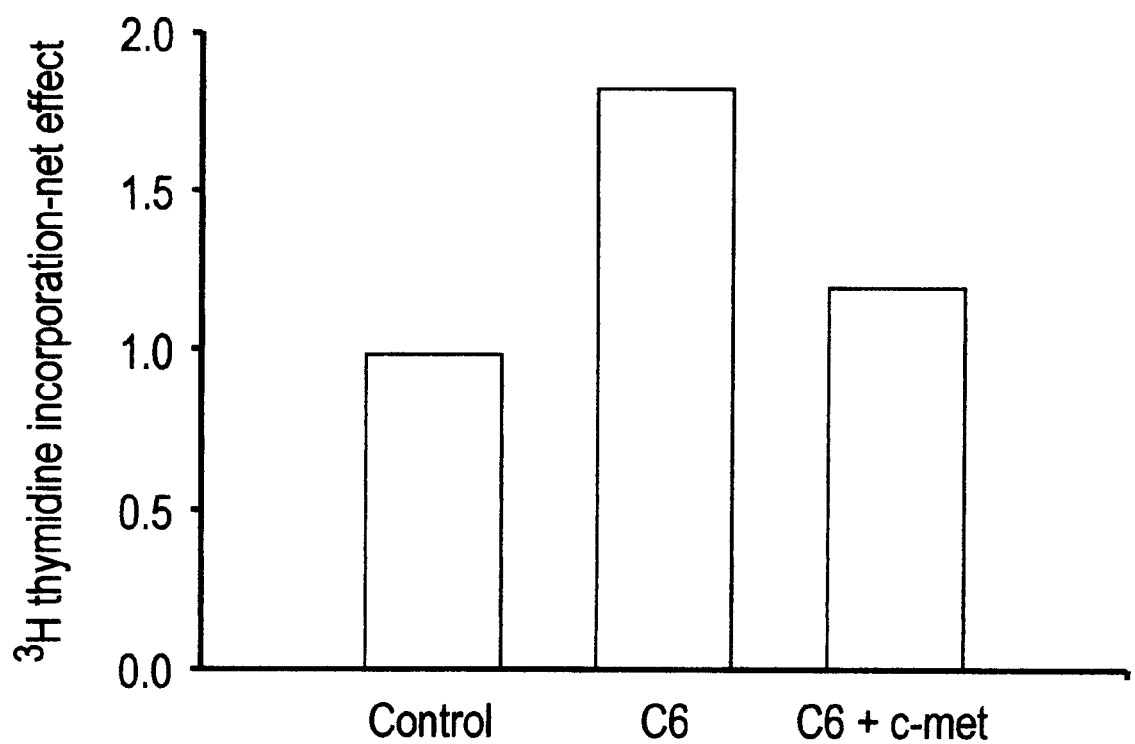
FIG. 1 depicts the stimulation of endothelial cell proliferation by (4-chlorophenyl)[3-(2-(2-thienyl)vinyl)-1H-pyrazol-1-yl]methanone, a compound of the invention with HGF/SF-like activity, and the inhibition of the observed stimulation by inclusion of c-Met.

The inventors herein have identified various small organic molecules of molecular weight below about 1,000 Daltons with the ability to either mimic or antagonize the biological activities of various growth factors that bind tyrosine kinase receptor growth factors, such as hepatocyte growth factor/scatter factor (HGF/SF), vascular endothelial growth factor (VEGF), and fibroblast growth factor (FGF). The present invention is directed to methods for the modulation of the various activities exhibited by such growth factors, for example, hepatocyte growth factor/scatter factor (HGF/SF), using small non-protein or non-peptide molecules. The inventors herein have identified for the first time small organic molecules that either mimic or have HGF/SF, VEGF or FGF activities, as well as those that are capable of inhibiting or antagonizing the activities of HGF/SF, VEGF and FGF. Thus, small molecule compounds having the HGF/SF-like or HGF/SF-inhibitory activities are described and their uses for the treatment of various conditions and diseases embraced herein. With the attendant difficulties in administering protein therapeutic agents at a desired level and for a duration effective to achieve acute and particularly chronic therapeutic goals, notwithstanding the cost of manufacture, the discovery by the inventors herein of small molecules with the desirable growth factor modulating activities offers pharmaceutically-desirable means to address a large number of conditions and diseases heretofore poorly or minimally treatable with available therapies.

Small-molecule, non-protein or non-peptide compounds with HGF/SF-like activity are characterized by one or more of the following activities: promoting proliferation of endothelial cells in vitro or in vivo, promoting angiogenesis in vitro or in vivo, promoting angiogenesis in wounds in vivo, promoting the growth of tumor cells in vitro or in vivo, promoting scatter, promoting anti-apoptotic activity, or inducing gene expression of angiogenic-cascade-related genes such as but not limited to IL-8 and angiopoietin-2. The modulator compounds of the invention, whether exhibiting HGF/SF-like activity, herein referred to interchangeably as HGF/SF agonist activity, or exhibiting HGF/SF inhibitory activity, herein referred to interchangeably as HGF/SF antagonist activity, are by theory acting through the HGF/SF receptor c-Met. While Applicants have no duty to disclose the theory by which the compounds of the invention are operating and are not bound thereto, the compounds of the invention modulate c-Met activity, and bind to c-Met. Preferred are compounds in which the aforementioned activity is inhibited or competed in the presence of exogenously-added c-Met receptor. The skilled artisan can readily identify such compounds by carrying out the foregoing assays as described in the examples below, and the present invention embraces the use of any and all such compounds for the purposes described herein.

In another broad aspect of the invention, compounds which antagonize HGF/SF activity have therapeutically-desirable properties for the treatment of conditions and diseases in which HGF/SF activity is undesirable. The use of any and all such small-molecule compounds is embraced herein. For example, abnormal cellular proliferation such as occurs in dysproliferative diseases such as various cancers and psoriasis, are such amenable conditions.

While the discussions herein describe the activities of HGF/SF agonists and antagonists, the skilled artisan will recognize, based on the studies described herein using other growth factors, that similar uses are afforded the agonists and antagonist compounds of the invention for these other growth factors.

Small-molecule, non-protein or non-peptide compounds with HGF/SF-antagonist activity are characterized by one or more of the following activities: inhibiting proliferation of endothelial cells in vitro or in vivo, inhibiting the growth, scatter or metastasis of tumor cells in vitro or in vivo, inhibiting scatter, or inhibiting anti-apoptotic activity. Preferred are compounds in which such activities are exhibitable in the presence of exogenously-added HGF/SF. The skilled artisan can readily identify such compounds by carrying out the foregoing assays as described in the examples below, and the present invention embraces the use of any and all such compounds for the purposes described herein.

The small organic molecules of the invention preferably have a molecular weight below 1,000 Daltons and more preferably of about 200 Daltons to about 1,000 Daltons; most preferably between about 300 Daltons and about 750 Daltons, and even most preferably between about 300 Daltons and about 500 Daltons. Moreover, the compounds preferably are not proteins or peptides, but may fall into any other class of organic molecule.

Compounds with HGF/SF activity are therapeutically useful for the treatment of numerous conditions and diseases in many but not all cases related to enhancement of cellular proliferation or vascular proliferation (angiogenesis). One aspect of the invention embraces the uses of the small molecule compounds described herein for the treatment of these conditions and diseases. These conditions and diseases are related to organ dysfunction and regeneration, reducing duration of wound healing, normalization of myocardial perfusion as a consequence of chronic cardiac ischemia or myocardial infarction, development or augmentation of collateral vessel development after vascular occlusion of or to ischemic tissues or organs, and vascularization of grafted or transplanted tissues, organs, or wound healing. These desired activities may be accelerated by administration of a compound of the invention. For example, promoting cellular proliferation, particularly of vascular cells, may be applied to the treatment of an ischemic, damaged or transplanted organ. Prophylaxis or treatment may be provided by contacting the tissue with an effective angiogenic amount of a compound of the invention. Contact may be provided by any appropriate means to deliver an effective amount of the agent for a duration to achieve the desired results. By way of non-limiting example, topical application may be applied to the desired target, or by infusion, bathing, or implantation of a sustained delivery device. For systemic administration, oral or parenteral routes may be employed. The target cells or tissue may be, for example, the liver or kidney, a transplanted or grafted tissue or organ such as skin, heart, vascular tissue or kidney, an ischemic organ, such as a heart following myocardial infarction or angina, a tissue or organ damaged by wounding, surgical intervention, vascular tissue, neural tissue, a wound, ulcer, etc. The cells may be, by way of non-limiting example, epithelial cells, endothelial cells, and smooth muscle cells, and tissues and organs comprising such cells. Promotion of growth and/or regeneration of neural tissue, teeth, and other tissues are embraced herein. Preferred cells, organs and tissues comprise the c-Met receptor. The aforementioned compounds with HGF/SF activity are also desirably useful for the treatment of various hepatic diseases including cirrhosis and liver failure; various renal diseases including renal failure. The compounds are also useful for inducing bone regeneration.

In one preferred embodiment, treatment of the endothelial cell dysfunction, vasculopathy and wound healing dysfunction that typifies diabetes mellitus is among the uses of the methods and compounds herein.

Thus, one aspect of the invention is directed to methods for the prophylaxis or treatment of a condition or disease in a mammal in which HGF/SF activity is desired or increased activity is desired comprising administering to the mammal an effective amount of a small-molecule compound with HGF/SF activity. The HGF/SF activity of a small-molecule compound of the invention is inhibited or blocked in the presence of or by preincubation with c-Met receptor.

In another broad aspect of the invention, compounds which antagonize HGF/SF activity have therapeutically-desirable properties for the treatment of conditions and diseases in which HGF/SF activity is undesirable. The use of any and all such small-molecule compounds is embraced herein. For example, abnormal cellular proliferation such as occurs in dysproliferative diseases such as various cancers and psoriasis, are such amenable conditions. Other conditions include inflammatory diseases, which exhibit a proliferative component, such as the intimal thickening and smooth muscle cell proliferation in atherosclerosis, among other inflammatory conditions.

Thus, another embodiment of the invention is directed to methods for the prophylaxis or treatment of a condition or disease in a mammal in which HGF/SF activity is not desired or decreased activity is desired comprising administering to the mammal an effective amount of a small-molecule compound with HGF/SF antagonist activity. The HGF/SF antagonist activity of a small-molecule HGF/SF antagonist compound of the invention may occur alone or only in the presence of exogenously-added HGF/SF or in cells or tissues in which HGF/SF is expressed.

Small-molecule, non-protein or non-peptide compounds with HGF/SF-antagonist activity are characterized by one or more of the following activities: inhibiting proliferation of endothelial cells in vitro or in vivo, inhibiting the growth of tumor cells in vitro or in vivo, inhibiting scatter of normal or tumor cells in vitro or in vivo, or inhibiting anti-apoptotic activity. Preferred are compounds in which such activities are exhibitable in the presence of exogenously-added HGF/SF. The skilled artisan can readily identify such compounds by carrying out the foregoing assays as described in the examples below, and the present invention embraces the use of any and all such compounds for the purposes described herein.

Moreover, and not to be bound by theory, the proliferation promoting compounds described above and antiproliferative compounds with the foregoing activities are believed to exert their effects by binding to and agonizing or antagonizing, respectively, the c-Met receptor present on numerous cell types within the body, comprising various tissues and organs, such cells including but not limited to epithelial cells, endothelial cells, fibroblasts, neuronal cells, and smooth muscle cells. Tissues and organs comprising such cell types are targets for the various activities described herein. As the effects of the agents herein on a single cell type comprising a tissue or organ may account for the therapeutic goal described, the agents herein may have profound effects on tissues or organs whose cells expressing c-Met comprise only a small fraction. The extent of expression of the target receptor does not detract from the utility of the agents and methods herein.

Conditions and diseases amenable to prophylaxis or treatment with the HGF/SF antagonist compounds of the invention include but are not limited to those in which abnormal vascular or cellular proliferation occurs. Such conditions and diseases include as in dysproliferative diseases including cancer and psoriasis, various inflammatory diseases characterized by proliferation of cells such as atherosclerosis and rheumatoid arthritis, and neovascularization in the eye as a consequence of diabetic retinopathy, suppression of cellular proliferation is a desired goal in the treatment of these and other conditions. As certain of the compounds of the invention have been found to possess antiproliferative activity on cells, as well as antiangiogenic activity, both activities may be beneficial in the treatment of, for example, solid tumors, in which both the dysproliferative cells and the enhanced tumor vasculature elicited thereby are targets for inhibition by the agents of the invention. In either case, therapy to promote or suppress proliferation may be beneficial locally but not systemically, and for a particular duration, and proliferation modulating therapies must be appropriately applied. The invention embraces localized delivery of such compounds to the affected tissues and organs, to achieve a particular effect.

Expression of scatter factor (HGF/SF), and its receptor, c-Met, is often associated with malignant progression (metastasis) of human tumors, including gliomas. Overexpression of HGF/SF in experimental gliomas enhances tumorigenicity and tumor-associated angiogenesis (i.e., growth of new blood vessels). More recent studies showed that human glioblastomas are HGF/SF-c-Met dependent and that a reduction in endogenous HGF/SF or c-Met expression can lead to inhibition of tumor growth and tumorigenicity. Thus, targeting the HGF/SF-c-Met signaling pathway using a compound as characterized above is an important approach in controlling tumor progression.

Examples of cancers, tumors, malignancies, neoplasms, and other dysproliferative diseases that can be treated according to the invention include leukemias such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The present invention is also directed to treatment of non-malignant tumors and other disorders involving inappropriate cell or tissue growth by administering a therapeutically effective amount of an agent of the invention. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperproliferative disorders is also contemplated. The agents may also be used topically to remove warts, birthmarks, moles, nevi, skin tags, lipomas, angiomas including hemangiomas, and other cutaneous lesions for cosmetic or other purposes.

As noted above, other uses of the compounds herein include intentional ablation or destruction of tissues or organs in a human or animal, for example, in the area of animal husbandry, and in the field of reproductive biology, to reduce the number of developing embryos; as an abortifacient, and as a means to achieve a biochemical castration, particularly for livestock and domesticated animals such as pets.

As mentioned above, vascularization of the vitreous humor of the eye as a consequence of diabetic retinopathy is a major cause of blindness, and inhibition of such vascularization is desirable. Other conditions in which vascularization is undesirable include certain chronic inflammatory diseases, in particular inflammatory joint and skin disease, but also other inflammatory diseases in which a proliferative response occurs and is responsible for part of all of the pathology. For example, psoriasis is a common inflammatory skin disease characterized by prominent epidermal hyperplasia and neovascularization in the dermal papillae. Proliferation of smooth muscle cells, perhaps as a consequence of growth factors, is a factor in the narrowing and occlusion of the macrovasculature in atherosclerosis, responsible for myocardial ischemia, angina, myocardial infarction, and stroke, to name a few examples. Peripheral vascular disease and arteriosclerosis obliterans comprise an inflammatory component. Numerous diabetic complications such as atherosclerosis, and particularly diabetic nephropathy, characterized by basement membrane thickening and mesangial cell proliferation, are believed to have a component of cellular proliferation attendant to excessive production of growth factors as a consequence of chronic hyperglycemia. These examples of proliferative diseases are given by way of illustration only, and the theoretical basis for their etiology as proliferative processes is not intended to be limiting to the invention, and applicants have no duty to disclose or be bound by such disclosure.

Moreover, localized ablation of tissues or even organs using antiproliferative or antiangiogenic compounds as characterized herein may find use in treatment of certain central nervous system diseases or conditions which otherwise may require dangerous invasive procedures; removal of cosmetically undesirable cutaneous lesions are further targets for the antiproliferative agents of the invention. In reproductive biology, such antiproliferative agents may be used as abortifacients or for non-surgical castration, particularly for use in livestock and domesticated animals. These are also merely illustrative of the uses of the instant agents.

The term "angiogenesis," as used herein, refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175–203 (1985)). These processes are controlled by soluble factors and by the extracellular matrix (see Ingber et al., Cell, Vol. 58, pp. 803–805 (1985)).

The foregoing discussions of the various uses of the growth factor agonist and antagonist compounds of the invention are not intended to be limited to those particular described conditions and diseases in which modulation of growth factor activity is desirable, but embraces those conditions and diseases for which increased or decreased growth factor activities are desirably modulated to achieve a benefit. One of skill in the art will be amply aware of the role of such growth factors in various conditions and disease and will be directed to the use of the compounds of the invention for the beneficial applications thereof. Various articles directed to such uses, incorporated herein in their entireties, are included below as a guide to such beneficial uses, but are merely illustrative and are not intended to be at all limiting.

The HGF/SF activity modulator compounds of the invention fall generally into four groups, as described below. As used herein, the term "alkyl" means straight-chain, branched-chain or cyclo saturated aliphatic hydrocarbon groups preferably containing from one to about 6 carbon atoms. Representative of such straight-chain groups are methyl, ethyl, butyl, pentyl, hexyl and the like. Examples of branched-chain groups include isopropyl, isobutyl and t-butyl. Cycloalkyl includes groups such as but not limited to cyclopropyl, cyclobutyl, cyclopentyl and cyclohexyl. The term "aryl" refers to, for example, phenyl, biphenyl and naphthyl groups, which are optionally substituted by one or more halogen (F, Cl, Br and I), C1 to C4 alkyl, or C1 to C4 alkyloxy, where alkyloxy refers to an alkyl group as defined above attached to the remainder of the molecule by oxygen. Examples of alkyloxy include methoxy, ethoxy, propoxy, isopropoxy and the like. The term "heteroaryl" refers to heterocyclic groups containing 4–10 ring members and 1–3 heteroatoms selected from the group consisting of oxygen, nitrogen and sulfur. Examples include but are not limited to isoxazolyl, phenylisoxazolyl, furyl, pyrimidinyl, quinolyl, tetrahydroquinolyl, pyridyl, imidazolyl, pyrrolidinyl, 1,2,4-triazoylyl, thiazolyl, thienyl, and the like. The aryl or heteroaryl group may be optionally substituted by one or more halogen (F, Cl, Br and I), C1 to C4 alkyl, C1 to C4 alkyloxy as described above, trifluoromethyl, difluoromethyl, nitro, hydroxy, amine (optionally alkyl substituted), or another aryl or another heteroaryl group as described above.

The organic compounds described herein with HGF/SF-like agonist or antagonist activity are merely illustrative of compounds which modulate one or more of the activities of HGF/SF and the uses of which are embraced herein.

Among the compounds and the formulae described below, certain of such compounds are known, and others are heretofore undescribed. The present invention embraces all such novel compounds with one or more of the activities hereindescribed, as well as pharmaceutical compositions comprising such compounds.

In one embodiment, the invention is directed to the use for any one or more of the aforementioned purposes of compounds that modulate HGF/SF activity with the general formula I:

Formula I

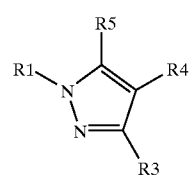

wherein
  R3 and R5 are independently or together a straight-chain or branched C1–C6 alkyl optionally substituted with a cyano or halogen, halogen, trifluoromethyl or difluoromethyl groups;
  R1 is hydrogen, methyl, CO-Aryl, SO$_2$-Aryl, CO-heteroaryl, or CO-alkyl; and
  R4 is CH$_2$-Aryl, halogen, arylcarbonylvinyl or S-heteroaryl.

The definitions of the substituents are as described hereinabove. R3 and R5 preferably may be methyl, t-butyl or chloro groups. The aryl group of substituent R1 is preferably an aromatic group such as phenyl, naphthyl, or biphenyl, substituted with one or more halogen, C1 to C4 alkyl or C1 to C4 alkyloxy groups. The heteroaryl group of substituent R1 preferably is a 3-aryl-substituted isoxazole or 3-aryl-substituted thienyl group. The alkyl group of substituent R1 preferably is t-butyl, or a C1–C6 straight, branched or cycloalkyl group. In a most preferred embodiment, R3 is methyl, R5 is chloro, R1 is methyl, and R4 is 4-chlorophenylcarbonylvinyl group.

Certain of the compounds of Formula I are novel, and the present invention is directed to all such novel compounds. The invention is also directed to a pharmaceutical composition comprising at least one compound of Formula I, in a pharmaceutically-acceptable carrier, for any of the uses described herein.

The invention is also directed to methods for the prophylaxis or treatment of a condition or disease in a mammal wherein the effects of HGF/SF would be beneficial by administering to the mammal an effective amount of a pharmaceutical composition comprising an active HGF/SF agonist of Formula I above. As mentioned above, such activities include but are not limited to promoting the proliferation of cells, including endothelial cells, vascular cells, hepatic cells, renal cells, among others; promoting angiogenesis; promoting vascularization; promoting wound healing and angiogenesis in wound healing, improving blood flow to ischemic tissues; and other desirable activities attendant to the desirable biological activities of endogenously-present or exogenously-administered HGF/SF. Those compounds of Formula I exhibiting HGF/SF antagonist activity, determinable readily by one of skill in the art, would be useful for the prophylaxis or treatment of a condition or disease in a mammal wherein the effects of HGF/SF would be undesirable, by administering to the mammal an effective amount of a pharmaceutical composition comprising an active HGF/SF antagonist of Formula I above. Such utilities include but are not limited to inhibition of angiogenesis or neovascularization, prevention of tumor growth or metastasis, inhibiting scatter, and inhibiting anti-apoptotic activities.

In a further embodiment, the invention is directed to methods for the prophylaxis or treatment of the aforementioned conditions and diseases using a therapeutically effective amount of a compound of Formula I whose HGF/SF-like activities are inhibited in the presence of, or by preincubation with, the HGF/SF receptor c-Met.

Non-limiting example of modulators of HGF/SF activity of Formula I include the following compounds, most of which, as will be seen in the examples below, exhibit HGF/SF agonist activity.

3-(5-chloro-1,3-dimethyl-1H-pyrazol-4-yl)-1-(4-chlorophenyl)prop-2-en-1-one [4-(2,6-dichlorobenzyl)-3,5-dimethyl-1H-pyrazol-1-yl][3-(2,6-dichlorophenyl)-5-methylisoxazol-4-yl]methanone (4-(2-chloro-6-fluorobenzyl)-3,5-dimethyl-1H-pyrazole-1-yl)(3-(2,6-dichlorophenyl)-5-methylisoxazol-4-yl)methanone 4-(2-chloro-6-fluorobenzyl)-1-((3,4-dichlorophenyl)sulfonyl)-3,5-dimethyl-1H-pyrazole 4-(2-chloro-6-fluorobenzyl)-1,3,5-trimethyl-1H-pyrazole 4-(2-chloro-6-fluorobenzyl)-3,5-dimethyl-1H-pyrazole (4-bromo-3,5-dimethyl-1H-pyrazol-1-yl)(3-(2,6-dichlorophenyl)isoxazole-4-carbohydrazide) 3-(4-(2,6-dichlorobenzyl)-3,5-dimethyl-1H-pyrazol-1-yl)propanenitrile 3,5-di(tert-butyl)-4-(2-chloro-6-fluorobenzyl)-1H-pyrazole (4-(2-chloro-6-fluorobenzyl)-3,5-dimethyl-1H-pyrazole-1-yl)(2,6-dichlorophenyl)methanone 1-(4-(2-chloro-6-fluorobenzyl)-3,5-dimethyl-1H-pyrazole-1-yl)2,2-dimethylpropan1-one (4-(2-chloro-6-fluorobenzyl)-3,5-dimethyl-1H-pyrazole-1-yl)(4-chlorophenyl)methanone (4-(2-chloro-6-fluorobenzyl)-3,5-dimethyl-1H-pyrazole-1-yl)(2-thienyl)methanone (4-chlorophenyl)(3,5-dimethyl-4-((1-methyl-1H-imidazol-2-yl)thio)-1H-pyrazol-1-yl)methanone In yet another embodiment, the invention is directed to the use for any one or more of the aforementioned purposes of compounds that modulate HGF/SF activity with the general formula II:

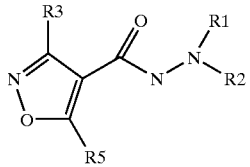

Formula II wherein

R5 is a C1 to C6 branched or straight-chained alkyl group;

R3 is a substituted or unsubstituted Aryl group;

R1 is hydrogen or a C1 to C4 straight-chained, branched or cycloalkyl group;

R2 is COCH$_2$ONCH-Aryl; heteroaryl, COCH$_2$CH$_2$Aryl; Aryl; COS-Aryl; CO-Heteroaryl; C1 to C4 straight-chained alkyl, branched alkyl, or cycloalkyl; or wherein R1 and R2 form a cyclic group of 5 or 6 carbon atoms.

The substituents are as defined hereinabove. Preferably, R5 is methyl. R3 is preferably an alkyl-, halogen- or alkyloxy-substituted phenyl group such as 2,6-dichlorophenyl. R1 is preferably hydrogen or methyl. R2 is preferably a substituted pyridyl group such as 2-(6-trifluoromethyl)pyridyl, a substituted arylthiocarbonyl group such as 2-(nitrophenyl)thiocarbonyl, or a 4-aryl-substituted-5-methylisoxazonecarbonyl group.

Most of the compounds of Formula II exhibit HGF/SF antagonist or inhibitory activity, as will be seen in the examples below. When R2 is COCH$_2$ONCH-Aryl, the compounds may exhibit agonist activity.

Certain of the compounds of Formula II are novel, and the present invention is directed to all such novel compounds. The invention is also directed to a pharmaceutical composition comprising at least one compound of Formula II, in a pharmaceutically-acceptable carrier, for any of the uses described herein.

Thus, this aspect of the invention is directed to method for the prophylaxis or treatment of a condition or disease in a mammal wherein the effects of HGF/SF would be undesirable, by administering to the mammal an effective amount of a pharmaceutical composition comprising an active HGF/SF antagonist of Formula II above. Such utilities include but are not limited to inhibition of angiogenesis or neovascularization, prevention of tumor growth or metastasis, inhibiting scatter, and inhibiting anti-apoptotic activities. As noted above, some compounds in Formula II exhibit HGF/SF-like activity and are likewise useful for the prophylaxis or treatment of a condition or disease in a mammal wherein the effects of HGF/SF would be beneficial by administering to the mammal an effective amount of a pharmaceutical composition comprising an active HGF/SF agonist of Formula II above. As mentioned above, such activities include but are not limited to promoting the proliferation of cells, including endothelial cells, vascular cells, hepatic cells, renal cells, among others; promoting angiogenesis; promoting vascularization; treatment of wound healing and endothelial cell dysfunction, improving blood flow to ischemic tissues; and other desirable activities attendant to the desirable biological activities of endogenously-present or exogenously-administered HGF/SF. The activity of a compound of Formula II would be readily determinable by one of skill in the art.

In a further embodiment, the invention is directed to methods for the prophylaxis or treatment of the aforementioned conditions and diseases using a therapeutically effective amount of a compound of Formula II whose HGF/SF antagonist activities occur in the presence of exogenously-added or endogenously produced HGF/SF, the latter within the cells or tissues.

Non-limiting examples of compounds of Formula II include:
N'4,5-dimethyl-N'4-(5-nitro-2-pyridyl)-3-(2,6-dichlorophenyl)isoxazole-4-carbohydrazide N'4-(2-(((2, 4-dichlorobenzylidene)amino)oxy)acetyl)-3-(2,6-dichlorophenyl)-5-methylisoxazole-4-carbohydrazide N'4-(3-(3,4,5-trimethoxyphenyl)propanoyl)-3-(2,6-dichlorophenyl)-5-methylisoxazole-4-carbohydrazide 2-nitrophenyl2-((3-(2,6-dichlorophenyl)-5-methylisoxazol-4-yl)carbonyl)hydrazine1-carbothioate N'4-((2-methyl1,3-thiazol-4-4yl)carbonyl)-3-(2,6-dichlorophenyl)-5-methylisoxazole-4-4carbohydrazide N1-((2-((3-(2,6-dichlorophenyl)-5-methylisoxazol-4-yl)carbonyl)hydrazino)(methylthio)methylidene)benzene1-sulfonamide N'4-(2,4,6-trichlorophenyl)-3-3(2,6-dichlorophenyl)-5-methylisoxazole-4-carbohydrazide N'4,3-di(2,6-dichlorophenyl)-5-methylisoxazole-4-carbohydrazide N'4-(3,5-dichloro-4-pyridyl)-3-(2,6-dichlorophenyl)-5-methylisoxazole-4-carbohydrazide N'4-phenyl-3-(2,6-dichlorophenyl)-5-methylisoxazole-4-carbohydrazide N'4,N'4,5-trimethyl-3-(2,6-dichlorophenyl)isoxazole-4-carbohydrazide N4-azepan1-yl-3-(2,6-dichlorophenyl)-5-methylisoxazole-4-carboxamide N'4-(6-(trifluoromethyl)-2-pyridyl)-3-(2,6-dichlorophenyl)-5-methylisoxazole-4-carbohydrazide N'4-(3,3-diethoxypropanoyl)-3-(2,6-dichlorophenyl)-5-methylisoxazole-4-carbohydrazide In still a further embodiment, the invention is directed to the use for the aforementioned purposes of compounds that modulate HGF/SF activity with the general formula III:

Formula III

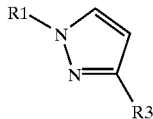

wherein
R1 is $SO_2$Alkyl, $SO_2$-Aryl, CO-t-Butyl, COAryl, CON-HAlkyl; CON-HAryl; and
R3 is CHCH-heteroaryl; phenoxyphenyl; heteroaryl; or Aryl substituted heteroaryl.

Preferably, R1 may be $SO_2$Alkyl, wherein Alkyl is C1 to C4 straight-chained, branched or cyclo, most preferably $SO_2CH_3$; $SO_2$-Aryl, wherein Aryl is halo, C1-4 alkyl or alkyloxy substituted phenyl; COAlkyl, wherein alkyl is C1 to C6 straight-chained alkyl, branched alkyl or cycloalkyl, most preferably CO-t-Butyl ; COAryl wherein Aryl is phenyl substituted with halo, C1-C4 alkyl or alkyloxy; CON-HAlkyl wherein alkyl is C1 to C6 straight-chained alkyl, branched alkyl or cycloalkyl, most preferably $CONHCH_3$; or CONHAryl, wherein aryl is phenyl substituted with halo, C1 to C4 alkyl or C1 to C4 alkyloxy. R3 may be CHCH-heteroaryl, where in heteroaryl includes but is not limited to both cis and trans CHCH-3-thienyl, CHCH-2-furyl and CHCH-3-furyl, and substituted CHCH-thienyl and CHCH-furyl, most preferably CHCH-2-thienyl; phenoxyphenyl; heteroaryl; or aryl substituted heteroaryl.

Certain of the compounds of Formula III are novel, and the present invention is directed to all such novel compounds. Moreover, the invention is also directed to a pharmaceutical composition comprising at least one compound of Formula III, in a pharmaceutically-acceptable carrier, for any of the uses described herein.

The invention is also directed to methods for the prophylaxis or treatment of a condition or disease in a mammal wherein the effects of HGF/SF would be beneficial by administering to the mammal an effective amount of a pharmaceutical composition comprising an active HGF/SF agonist of Formula III above. As mentioned above, such activities include but are not limited to promoting the proliferation of cells, including endothelial cells, vascular cells, hepatic cells, renal cells, among others; promoting angiogenesis; promoting vascularization; improving or enhancing wound healing; treating endothelial cell dysfunction; improving blood flow to ischemic tissues; and other desirable activities attendant to the desirable biological activities of endogenously-present or exogenously-administered HGF/SF. Those compounds of Formula III exhibiting HGF/SF antagonist activity, determinable readily by one of skill in the art, would be useful for the prophylaxis or treatment of a condition or disease in a mammal wherein the effects of HGF/SF would be undesirable, by administering to the mammal an effective amount of a pharmaceutical composition comprising an active HGF/SF antagonist of Formula III above. Such utilities include but are not limited to inhibition of angiogenesis or neovascularization, prevention of tumor growth or metastasis, inhibiting scatter, and inhibiting anti-apoptotic activities.

In a further embodiment, the invention is directed to methods for the prophylaxis or treatment of the aforementioned conditions and diseases using a therapeutically effective amount of a compound of Formula III whose HGF/SF-like activities are inhibited in the presence of, or by preincubation with, the HGF/SF receptor c-Met.

These compounds generally exhibit HGF/SF stimulatory or agonist activity. Non-limiting examples of compounds of Formula III include
(4-chlorophenyl)[3-(2-(2-thienyl)vinyl)-1H-pyrazol-1-yl]methanone; 1-(methylsulfonyl)-3-(2-(2-thienyl)vinyl)-1H-pyrazole 2,2-dimethyl-1-(3-(2-(2-thienyl)vinyl)-1H-pyrazole-1-yl)propan1-one N-methyl-3-(2-(2-thienyl)vinyl)-1H-pyrazole-1-carboxamide (4-chlorophenyl)(3-(3-phenylisoxazol-5-yl)-1H-pyrazol-1-yl)methanone (4-chlorophenyl)(3-(3-(4-chlorophenyl)-5-methylisoxazol-4-yl)-1H-pyrazol-1-yl)methanone (4-chlorophenyl)(3-(5-(2-thienyl)-2-thienyl)-1H-pyrazol-1-yl)methanone (2,4-dichlorophenyl)(3-(5-(2,4-difluorophenyl)-2-furyl)-1H-pyrazol-1-yl)methanone N1-phenyl-3-(2-(2-thienyl)vinyl)-1H-pyrazole-1-carboxamide (4-chlorophenyl)(3-(2-(5-(2-thienyl)-2-thienyl)-4-methyl-1,3-thiazol-5-yl)-1H-pyrazol-1-yl)methanone (3-benzhydryl-1H-pyrazol-1-yl)(4-chlorophenyl)methanone N1-(4-chlorophenyl)-3-(2-(2-thienyl)vinyl)-1H-pyrazole-1-carboxamide (4-chlorophenyl)(3-(2-methylimidazo(1,2-a)pyridin-3-yl)-1H-pyrazol-1-yl)methanone 2-chloro-6-(4-(1-(4-chlorobenzyl)-1H-pyrazol-3-yl)phenoxy)benzonitrile 1-((4-chlorophenyl)sulfonyl)-3-(2-(2-thienyl)vinyl)-1H-pyrazole In a further embodiment, the invention is directed to the use for any one or more of the aforementioned purposes of compounds that modulate HGF/SF activity with the general formula IV:

Formula IV

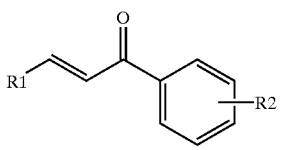

Wherein
R1 is Aryl or Heteroaryl; and
R2 is one or more halogen, nitro, C1 to C4 straight-chained alkyl, branched alkyl, or cycloalkyl, or C1 to C4 alkyloxy groups.

The definitions of the aforementioned substituents are described hereinabove. Preferably, R1 is a phenyl group substituted with one or more halogen, C1 to C4 alkyl, or C1 to C4 alkyloxy groups, or a heteroaryl, most preferably 4-bromo-2-thienyl, 4-pyridyl, 2-furyl, 3-thienyl, substituted with halogens and/or C1 to C4 alkyl. R2 preferably is halogen (F, Cl, Br), nitro, or a C1 to C4 straight-chained alkyl, branched alkyl, or cycloalkyl group or a C1 to C4 alkyloxy group; most preferably, R2 is a methyl group and a chloro group.

Certain of the compounds of Formula IV are novel, and the present invention is directed to all such novel compounds. In addition, the invention is also directed to a pharmaceutical composition comprising at least one compound of Formula IV, in a pharmaceutically-acceptable carrier, for any of the uses described herein.

Certain compounds of Formula IV exhibit HGF/SF agonist activity and others exhibit HGF/SF antagonist activity. The skilled artisan may readily determine the activity of the compounds, and the dose at which the compound exhibits such activity. Thus, the invention is also directed to methods for the prophylaxis or treatment of a condition or disease in a mammal wherein the effects of HGF/SF would be beneficial by administering to the mammal an effective amount of a pharmaceutical composition comprising an active HGF/SF agonist of Formula IV above. As mentioned above, such activities include but are not limited to promoting the proliferation of cells, including endothelial cells, vascular cells, hepatic cells, renal cells, among others; promoting angiogenesis; promoting vascularization; improving wound healing,; improving vascularization of wounds; improving endothelial cell dysfunction; improving blood flow to ischemic tissues; and other desirable activities attendant to the desirable biological activities of endogenously-present or exogenously-administered HGF/SF. Those compounds of Formula IV exhibiting HGF/SF antagonist activity, determinable readily by one of skill in the art, would be useful for the prophylaxis or treatment of a condition or disease in a mammal wherein the effects of HGF/SF would be undesirable, by administering to the mammal an effective amount of a pharmaceutical composition comprising an active HGF/SF antagonist of Formula IV above. Such utilities include but are not limited to inhibition of angiogenesis or neovascularization, prevention of tumor growth or metastasis, inhibiting scatter, and inhibiting anti-apoptotic activities.

In a further embodiment, the invention is directed to methods for the prophylaxis or treatment of the aforementioned conditions and diseases using a therapeutically effective amount of a compound of Formula IV whose HGF/SF-like activities are inhibited in the presence of, or by preincubation with, the HGF/SF receptor c-Met. The antagonist activity of an HGF/SF antagonist compound of Formula IV may be active alone, or may be active in the presence of either exogenously-administered HGF/SF or in cells or tissues in which HGF/SF is expressed or induced to be expressed.

The compounds in this group may be HGF/SF agonists or antagonists. Non-limiting examples of modulators of Formula IV include:
1-(4-chloro-3-methylphenyl)-3-(2,6-dichlorophenyl)-prop-2-en-1-one 1-(4-chloro-3-methylphenyl)-3-(2-chlorophenyl)prop-2-en-1-one 3-(2-chloro-6-fluorophenyl)-1-(4-chloro-3-methylphenyl)prop-2-en-1-one 3-(4-bromo-2-thienyl)-1-(3,4-dichlorophenyl)prop-2-en-1-one 3-(4-bromo-2-thienyl)-1-(4-chloro-3-methylphenyl)prop-2-en-1-one 3-(4-bromo-2-thienyl)-1-(4-fluorophenyl)prop-2-en-1-one 3-(4-bromo-2-thienyl)-1-(4-chlorophenyl)prop-2-en-1-one 1-(4-chlorophenyl)-3-(2,4-dichlorophenyl)prop-2-en-1-one 3-(1,3-benzodioxol-5-yl)-1-(4-bromophenyl)prop-2-en-1-one 3-(3-phenoxy-2-thienyl)-1-(2-thienyl)prop-2-en-1-one 3-(3-bromo-4-methoxyphenyl)-1-phenylprop-2-en-one 3-(3,4-dichlorophenyl)-1-(2-nitrophenyl)prop-2-en-1-one 1-(4-chlorophenyl)-3-(3,4-dichlorophenyl)prop-2-en-1-one 1-(4-chlorophenyl)-3-(3,5-dichloro-2-hydroxyphenyl)prop-2-en-1-one 1-(2-chlorophenyl)-3-(3,5-dichloro-2-hydroxyphenyl)prop-2-en-1-one 3-(4-chlorophenyl)-1-(2,6-dichlorophenyl)prop-2-en-1-one 1-(4-bromophenyl)-3-(4-chlorophenyl)prop-2-en-1-one 1-(2-chlorophenyl)-3-(2,6-dichlorophenyl)prop-2-en-1-one 1-(4-chlorophenyl)-3-(2,6-dichlorophenyl)prop-2-en-1-one 3-(2,6-dichlorophenyl)-1-(4-methoxyphenyl)prop-2-en-1-one 3-(4-chloro-1-methyl-1H-pyrazol-3-yl)-1-[4-(trifluoromethyl)phenyl]prop-2-en-1-one 3-(2,4-dichlorophenyl)-1-(2-methylphenyl)prop-2-en-1-one 3-(2,6-dichlorophenyl)-1-(2-methylphenyl)prop-2-en-1-one 3-(3,4-dichlorophenyl)-1-(2-methylphenyl)prop-2-en-1-one 3-(5-bromo-2-hydroxyphenyl)-1-(3-methylphenyl)prop-2-en-1-one 3-(5-bromo-2-hydroxyphenyl)-1-(4-methylphenyl)prop-2-en-1-one 3-(2,4-dichlorophenyl)-1-(3-methylphenyl)prop-2-en-1-one 3-(2,4-dichlorophenyl)-1-(4-methoxyphenyl)prop-2-en-1-one 1-[4-amino-2-(methylthio)-1,3-thiazol-5-yl]-3-(4-chlorophenyl)prop-2-en-1-one 1-(4-chlorophenyl)-3-[4-(trifluoromethyl)phenyl]prop-2-en-1-one 1-benzo[b]thiophen-3-yl-3-(4-chlorophenyl)prop-2-en-1-one 1,3-di (5-nitro-3-thienyl)prop-2-en-1-one 1-(4-bromophenyl)-3-(3,5-difluorophenyl)prop-2-en-1-one 3-(3,5-difluorophenyl)-1-(3-nitrophenyl)prop-2-en-1-one The compounds of Formulae I–IV described above may be synthesized and isolated following standard methods readily available to one skilled in the art of synthetic organic chemistry. Moreover, the compounds may be readily prepared at a purity acceptable for administration to a mammal, preferably a human, at a dose effective to prophylax or treat any of the conditions and diseases related to the desired or undesired activities of HGF/SF as mentioned above.

The following discussion is applicable to all of the various aspects of the invention described herein.

The compounds of the invention may be administered to the desired site in the body or target tissue or organ by any means that achieves the desired therapeutic effect. By way of non-limiting example, compounds with HGF/SF activity, including proliferation-promoting agents including angiogenic agents, may be administered locally, such as by injection or deposition in a target tissue or organ, or by the implantation of a controlled release delivery device or matrix containing the compound, to achieve local effects. For enhanced healing of wounds, such as diabetic wounds including foot ulcers, the compounds of the invention may be applied topically. Other sites may be accessed surgically, or via transcutaneous catheterization to gain access to a tissue or organ through the major vasculature. For example, enhancing the perfusion of the ischemic heart may be achieved by use of a transcutaneous catheter that may be positioned to release the HGF/SF mimic/angiogenic compound of the invention into the coronary vasculature.

For antiproliferative agents including antiangiogenic (angiostatic) agents, local administration of an compound at the desired site of activity, such as a tumor or the vitreous humor, may be carried out, or implantation of a controlled release delivery device containing an agent of the invention in the tumor or eye, may be desirable to achieve local effects. Surgical or transcutaneous methods may also be used. These and other means for contacting a compound of the invention with the desired target cells, tissue or organs will be readily apparent to the skilled artisan.

In yet another aspect of the present invention, provided herein are pharmaceutical compositions of any and all the above compounds. Such pharmaceutical compositions comprise at least one of the compounds herein, together with a pharmaceutically-acceptable carrier.

As noted above, the application and duration of application of the compounds of the invention may require particular local placement or delivery, for example, exposure of the antiproliferative compounds to a solid tumor or within the vitreous humor; and avoidance, for example, of systemic exposure. Exposure of proliferation-promoting compounds such as angiogenic compounds to a transplanted or ischemic tissue or organ is desirable without exposing such agents to other sites in the body. Such considerations, depending on the target cells, tissues or organs, whether the therapy is to promote or suppress proliferation, and the duration of exposure, may be determined readily by the skilled artisan. The formulation of the instant compounds in appropriate vehicles or carriers or drug delivery systems is also determinable by the skilled artisan, and all such methods of delivery are embraced herein. Examples are provided herein by way of illustration only, and are not intended to be limiting whatsoever.

Such pharmaceutical compositions may be for administration to a particular site by injection, catheterization or implantation, but may also be delivered for certain uses by other routes including oral, pulmonary, nasal or other forms of administration. In general, comprehended by the invention are pharmaceutical compositions comprising effective amounts of an agent or agents, or derivative products, of the invention together with pharmaceutically acceptable diluents, preservatives, solubilizers, emulsifiers, adjuvants and/or carriers. Such compositions may include diluents of various buffer content (e.g., Tris-HCl, acetate, phosphate), pH and ionic strength; additives such as detergents and solubilizing agents (e.g., Tween 80, Polysorbate 80), antioxidants (e.g., ascorbic acid, sodium metabisulfite), preservatives (e.g., Thimersol, benzyl alcohol) and bulking substances (e.g., lactose, mannitol). The foregoing examples are merely illustrative and non-limiting, as the skilled artisan will be amply aware of suitable excipients and other component of a pharmaceutical composition comprising one or more agents of the invention.

For controlled delivery, incorporation of the material into particulate preparations of polymeric compounds such as polylactic acid, polyglycolic acid, etc. or into liposomes may be used, or the use of a controlled release device, such as an implantable osmotic or other type of pump. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Likewise, the skilled artisan will be amply aware of suitable delivery methods that may be extended to the agents of the invention to achieve the intended therapeutic goals of the invention. Such local release may be desirably, for example, with antiproliferative agents for treatment of a tumor or abnormal vascularization in the eye; and proliferative agents at the site of grafts or transplants.

While the foregoing discussions have been directed principally to the compounds useful for the promotion or inhibition of HGF/SF activity, and its receptor c-Met, they are generally applicable to agonists and antagonists of other growth factors, particularly growth factors whose activities involve binding to a tyrosine kinase receptor.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Assay Methods

The following assays were used to evaluate the activity of the various compounds discussed herein. Certain of the compounds and groups thereof express-like activity, i.e., they induce scatter, cell proliferation, inhibit apoptosis, among other activities, and if acting through the c-Met receptor, agonize or stimulate c-Met receptor activity. The specificity for such compounds working through the c-Met receptor may be identified by performing the stimulation assay in the presence of free c-Met receptor. Reduction of a proliferative response in the presence of c-Met indicates such specificity.

To evaluate inhibitors of activity, compounds may be evaluated directly for anti-proliferative activities, such as the inhibition of cellular proliferation, inhibition of tumor growth, inhibition of scatter, and inhibition of gene expression, and may also be evaluated on their ability to inhibit activity when exposed to cells together with. In such instances, the scatter and/or proliferative activities induced by added will be inhibited by the attendant presence of an inhibitory compound of the invention. Thus, certain inhibitors may be inhibitory in the absence of exogenously-added; these and/or other compounds may exhibit inhibitory activity only in the presence of.

It is noted that Applicants have no duty to disclose the theory or mechanism by which or through the compounds of the invention operate, nor are they in any way bound by such disclosure.

Cell proliferation assays Endothelial cells (HUVECs) were seeded in 48 well plates at a density of 10,000 to 20,000 cells per well in the normal growth medium (EGM-2-Clonetics) containing 2% fetal bovine serum, FGF, VEGF, IGF, ascorbic acid, EGF, GA, heparin and hydrocortisone. The cells were grown normally in the growth medium for 24 hr at 37 degrees C and 5% $CO_2$. The cells were then rinsed with RPMI-1% BSA and starved for 1–2 hrs. The stock solutions of all the compounds were made at a concentration of 10 mg/ml in DMSO and diluted in RPMI-1% BSA at a final concentrations of 1 to 12 microgram/ml. The cells were then washed and treated with the compounds and incubated for another 24 hr at 37 degrees C. Then $^3$H thymidine (0.5 microgram/ml in RPMI-BSA) was added to the cells and incubated at 37 degrees C. for 4 to 5 hours. The unincorporated thymidine was removed by washing the cells four times with 1×PBS. Then the cells were lysed with 0.5M NaOH for 30 min and the radioactivity counted in the beta counter.

In other experiments, human iliac artery endothelial cells were used under similar conditions as those described above.

Effect on growth of tumor cells. The activity of the compounds herein to promote or inhibit the growth of tumor cells was evaluated using human endometrial cancer cells.

Scatter Assay. A standard assay for scatter of MDCK cells was performed. Results were evaluated by microscopic examination.

Anti-apoptotic Activity Assay. The ability of compounds of the present invention to protect cells from apoptosis was performed using a MTT viability assay with MDCK cells exposed to adriamycin (15 micromolar) to induce apoptosis. HGF/SF was evaluated as a positive control.

Effect of the compounds on gene expression patterns. Additional data on the cellular effects of the compounds of the invention was obtained from GeneChip studies. In particular, effects on induction of angiogenic-cascade-related genes including interleukin-8 and angiopoietin-2 were evaluated.

EXAMPLE 2

Compounds

The following compounds were evaluated for activities herein.
(4-chlorophenyl)[3-(2-(2-thienyl)vinyl)-1H-pyrazol-1-yl]methanone (C16H11CIN2OS/315) 1-(methylsulfonyl)-3-(2-(2-thienyl)vinyl)-1H-pyrazole 2,2-dimethyl-1-(3-(2-(2-thienyl)vinyl)-1H-pyrazol-1-yl)propan-1-one (4-chlorophenyl)(3,5-di(tert-butyl)-1H-pyrazol-1-yl) methanone N-methyl-3-(2-(2-thienyl)vinyl)-1H-pyrazole-1-carboxamide 1-(4-chlorobenzoyl)-5-cyclopropyl1H-pyrazole-4-carbonitrile (4-chlorophenyl)(3-(3-phenylisoxazol-5-yl)-1H-pyrazol-1-yl)methanone 5-(2-(2-thienyl)vinyl)-1H-pyrazole ethyl 1-(4-chlorobenzoyl)-3-methyl-1H-pyrazol-5-carboxylate (4-chlorophenyl)(3,5-dimethyl-4-(pyrimidin-2-ylthio)-1H-pyrazol-1-yl)methanone (4-chlorophenyl)(3-(3-(4-chlorophenyl)-5-methylisoxazol-4-yl)-1H-pyrazol-1-yl)methanone (4-chlorophenyl)(3-(5-(2-thienyl)-2-thienyl)-1H-pyrazol-1-yl)methanone (2,4-dichlorophenyl)(3-(5-(2,4-difluorophenyl)-2-furyl)-1H-pyrazol-1-yl)methanone (4-(2-chloro-6-fluorobenzyl)-3,5-dimethyl-1H-pyrazol-1-yl)(4-chlorophenyl)methanone methyl 4-(1-(4-chlorobenzoyl)-1H-pyrazol-5-yl)-5-methylisoxazole-3-carboxylate (4-chlorophenyl)(5-(methylthio)-3-(4-phenoxyphenyl)-1H-pyrazol-1-yl) methanone (4-chlorophenyl)(3,5-dimethyl-4-((1-methyl-1H-imidazol-2-yl)thio)-1H-pyrazol-1-yl)methanone N1-phenyl-3-(2-(2-thienyl)vinyl)-1H-pyrazole-1-carboxamide (4-chlorophenyl)(3-(2-(5-(2-thienyl)-2-thienyl)-4-methyl-1,3-thiazol-5-yl)-1H-pyrazol-1-yl)methanone (4-chlorophenyl)(3,5-dimethyl-4-phenoxy-1H-pyrazol-1-yl)methanone (3-benzhydryl-1H-pyrazol-1-yl)(4-chlorophenyl)methanone (4-chlorophenyl)(3,5-dimethyl-4-((5-(trifluoromethyl)-2-pyridyl)thio)-1H-pyrazol-1-yl)methanone N1-(4-chlorophenyl)-3-(2-(2-thienyl)vinyl)-1H-pyrazole-1-carboxamide methyl 1-(4-chlorobenzoyl)-5-(dimethoxymethyl)-1H-pyrazole-4-carboxylate (4-chlorophenyl)(3-(2-methylimidazo(1,2-a)pyridin-3-yl)-1H-pyrazol-1-yl)methanone (4-chlorophenyl)(3,5-dimethyl-4-)((1-phenyl-1H1,2,3,4-tetraazol-5-yl)thio)-1H-pyrazol-1-yl)methanone methyl 1-(4-chlorobenzoyl)-5-isoxazol-5-yl-3-methyl-1H-pyrazole-4-carboxylate (3-(tert-butyl)5-(methylthio)-1H-pyrazol-1-yl)(4-chlorophenyl)methanone 2-chloro-6-(4-(1-(4-chlorobenzyl)-1H-pyrazol-5-yl)phenoxy) benzonitrile (4-chlorophenyl)(5-(5-methyl-3-phenylisoxazol-4-yl)-1H-pyrazol-1-yl) methanone 1-((4-chlorophenyl)sulfonyl)-3-(2-(2-thienyl)vinyl)-1H-pyrazole (4-chlorophenyl)(3,5-dimethyl-4-((4-methyl-5-(trifluoromethyl)-4H-1,2,4-triazol-3-yl)thio)-1H-pyrazol-1-yl)methanone methyl 1-(4-chlorobenzoyl)-3-methyl-5-(4-methyl-1,2,3-thiadiazol-5-yl)-1H-pyrazole-4-carboxylate
[4-(2,6-dichlorobenzyl)-3,5-dimethyl-1H-pyrazol-1-yl][3-(2,6-dichlorophenyl)-5-methylisoxazol-4-yl]methanone (C23H17C14N302/509) 4-(2-chloro-6-fluorobenzyl)-3,5-dimethyl-1-(phenylsulfonyl)-1H-pyrazole (4-(2-chloro-6-fluorobenzyl)-3,5-dimethyl-1H-pyrazole-1-yl)(3-(2,6-dichlorophenyl)-5-methylisoxazol-4-yl)methanone 4-(2-chloro-6-fluorobenzyl)-1-((3,4-dichlorophenyl)sulfonyl)-3,5-dimethyl-1H-pyrazole 4-(2-chloro-6-fluorobenzyl)-1,3,5-trimethyl-1H-pyrazole 4-(2-chloro-6-fluorobenzyl)-3,5-dimethyl-1H-pyrazole (4-bromo-3,5-dimethyl-1H-pyrazol-1-yl)(3-(2,6-dichlorophenyl)isoxazole-4-carbohydrazide) N'4,5-dimethyl-N'4-(5-nitro-2-pyridyl)-3-(2,6-dichlorophenyl)isoxazole-4-carbohydrazide N'4-(2-(((2,4-dichlorobenzylidene)amino)oxy)acetyl)-3-(2,6-dichlorophenyl)-5-methylisoxazole-4-carbohydrazide 3-(2,6-dichlorophenyl)-5-methylisoxazole-4-carbohydrazide N'4-(3-(3,4,5-trimethoxyphenyl)propanoyl)-3-(2,6-dichlorophenyl)-5-methylisoxazole-4-carbohydrazide 2-nitrophenyl 2-((3-(2,6-dichlorophenyl)-5-methylisoxazol-4-yl)carbonyl)hydrazine-1-carbothioate 4-(2,6-dichlorobenzyl)-1-((3,5-di(trifluoromethyl)phenyl)sulfonyl)-3,5-dimethyl-1H-pyrazole 1-((4-chlorophenyl)sulfonyl)-4-(2,6-dichlorobenzyl)-3,5-dimethyl-1H-pyrazol (4-(2,6-dichlorobenzyl)-3,5-dimethyl-1H-pyrazol-1-yl)(2,6-dichlorophenyl)methanone 3-(4-(2,6-dichlorobenzyl)-3,5-dimethyl-1H-pyrazol-1-yl)propanenitrile N'4-((2-methyl-1,3-thiazol-4-4yl)carbonyl)-3-(2,6-dichlorophenyl)-5-methylisoxazole-4-4carbohydrazide N1-((2-((3-(2,6-dichlorophenyl)-5-methylisoxazol-4-yl)carbonyl)hydrazino)(methylthio)methylidene)benzene1-sulfonamide N'4-(2,4,6-trichlorophenyl)-3-3(2,6-dichlorophenyl)-5-methylisoxazole-4-carbohydrazide N'4,3-di(2,6-dichlorophenyl)-5-methylisoxazole-4-carbohydrazide 3,5-di(tert-butyl)-4-(2-chloro-6-fluorobenzyl)-1H-pyrazole N'4-(3,5-dichloro-4-pyridyl)-3-(2,6-dichlorophenyl)-5-methylisoxazole-4-carbohydrazide N'4-phenyl-3-(2,6-dichlorophenyl)-5-methylisoxazole-4-carbohydrazide (4-(2-chloro-6-fluorobenzyl)-3,5-dimethyl-1H-pyrazole-1-yl)(2,6-dichlorophenyl)methanone 1-(4-(2-chloro-6-fluorobenzyl)-3,5-dimethyl-1H-pyrazole-1-yl)-2,2-dimethylpropan-1-one N'4,N'4,5-trimethyl-3-(2,6-dichlorophenyl)isoxazole-4-carbohydrazide N4-azepan-1-yl-3-(2,6-dichlorophenyl)-5-methylisoxazole-4-carboxamide N'4-(6-(trifluoromethyl)-2-pyridyl)-3-(2,6-dichlorophenyl)-5-methylisoxazole-4-carbohydrazide (4-(2-chloro-6-fluorobenzyl)-3,5-dimethyl-1H-pyrazole-1-yl)(4-chlorophenyl)methanone N4Piperidino-3-(2,6- dichlorophenyl)-5methylisoxazole-4-carboxamide N'4-(3,3-diethoxypropanoyl)-3-(2,6-dichlorophenyl)-5-methylisoxazole-4-carbohydrazide (4-(2-chloro-6-fluorobenzyl)-3,5-dimethyl-1H-pyrazole-1-yl)(2-thienyl)methanone N'4-(2,5-dichlorophenyl)-3-(2,6-dichlorophenyl)-5-methylisoxazole-4-carbohydrazide 1-(4-chloro-3-methylphenyl)-3-(2,6-dichlorophenyl)-prop-2-en-1-one 1-(4-chloro-3-methylphenyl)-3-(2-chlorophenyl)prop-2-en-1-one 3-(2-chloro-6-fluorophenyl)-1-(4-chloro-3-methylphenyl)prop-2-en-1-one 3-(4-bromo-2-thienyl)-1-(3,4-dichlorophenyl)prop-2-en-1-one 3-(4-bromo-2-thienyl)-1-(4-chloro-3-methylphenyl)prop-2-en-1-one 3-(4-bromo-2-thienyl)-1-(4-fluorophenyl)prop-2-en-1-one 3-(4-bromo-2-thienyl)-1-(4-chlorophenyl)prop-2-en-1-one 1-(4-chlorophenyl)-3-(2,4-dichlorophenyl)prop-2-en-1-one 3-(1,3-benzodioxol-5-yl)-1-(4-bromophenyl)prop-2-en-1-one 3-(3-phenoxy-2-thienyl)-1-(2-thienyl)prop-2-en-1-one 3-(3-bromo-4-methoxyphenyl)-1-phenylprop-2-en-one 3-(3,4-dichlorophenyl)-1-(2-nitrophenyl)prop-2-en-1-one 1-(4-chlorophenyl)-3-(3,4-dichlorophenyl)prop-2-en-1-one 1-(4-chlorophenyl)-3-(3,5-dichloro-2-hydroxyphenyl)prop-2-en-1-one 1-(2-chlorophenyl)-3-(3,5-dichloro-2-hydroxyphenyl)prop-2-en-1-one 3-(4-chlorophenyl)-1-(2,6-dichlorophenyl)prop-2-en-1-one 1-(4-bromophenyl)-3-(4-chlorophenyl)prop-2-en-1-one 1-(2-chlorophenyl)-3-(2,6-dichlorophenyl)prop-2-en-1-one 1-(4-chlorophenyl)-3-(2,6-dichlorophenyl)prop-2-en-1-one 3-(2,6-dichlorophenyl)-1-(4-methoxyphenyl)prop-2-en-1-one 3-(4-chloro-1-methyl-1H-pyrazol-3-yl)-1-[4-(trifluoromethyl)phenyl]prop-2-en-1-one 3-(2,4-dichlorophenyl)-1-(2-methylphenyl)prop-2-en-1-one 3-(2,6-dichlorophenyl)-1-(2-methylphenyl)prop-2-en-1-one 3-(3,4-dichlorophenyl)-1-(2-methylphenyl)prop-2-en-1-one 3-(2,6-dichlorophenyl)-1-(3-methylphenyl)prop-2-en-1-one 3-(5-bromo-2-hydroxyphenyl)-1-(3-methylphenyl)prop-2-en-1-one 3-(5-bromo-2-hydroxyphenyl)-1-(4-methylphenyl)prop-2-en-1-one 3-(2,4-dichlorophenyl)-1-(3-methylphenyl)prop-2-en-1-one 3-(2,4-dichlorophenyl)-1-(4-methoxyphenyl)prop-2-en-1-one 1-[4-amino-2-(methylthio)-1,3-thiazol-5-yl]-3-(4-chlorophenyl)prop-2-en-1-one 1-(4-chlorophenyl)-3-[4-(trifluoromethyl)phenyl]prop-2-en-1-one 1-benzo[b]thiophen-3-yl-3-(4-chlorophenyl)prop-2-en-1-one 1,3-di(5-nitro-3-thienyl)prop-2-en-1-one 1-(4-methyl-2-(3-thienyl)-1,3-thiazol-5-yl]-3-(2-thienyl)prop-2-en-1-one 1-(4-bromophenyl)-3-(3,5-difluorophenyl)prop-2-en-1-one 3-(3,5-difluorophenyl)-1-(3-nitrophenyl)prop-2-en-1-one

EXAMPLE 3

HGF/SF-Like Cellular Proliferative Activity of a Compound of the Invention

Using the endothelial cell proliferation assay described above, the compound (4-chlorophenyl)[3-(2-(2-thienyl)vinyl)-1H-pyrazol-1-yl]methanone was shown to increase HUVEC proliferation by two to five fold. The specificity of the stimulation of endothelial cell growth by the compound as measured by $^3$H-thymidine incorporation was tested by pre-incubation of cells with the HGF/SF receptor c-met. In FIG. 1, the first bar represents control cells; the second bar (4-chlorophenyl)[3-(2-(2-thienyl)vinyl)-1H-pyrazol-1-yl]methanone at 6 microgram/ml; and the third bar: (4-chlorophenyl)[3-(2-(2-thienyl)vinyl)-1H-pyrazol-1-yl] methanone at 6 microgram/ml plus c-Met receptor, 100 microgram/ml. (4-Chlorophenyl)[3-(2-(2-thienyl)vinyl)-1H-pyrazol-1-yl]methanone by itself stimulated $^3$H-thymidine incorporation by 84%. Thus, (4-chlorophenyl)[3-(2-(2-thienyl)vinyl)-1H-pyrazol-1-yl]methanone is as effective as HGF/SF in stimulating HUVEC proliferation. In the presence of c-Met, the (4-chlorophenyl)[3-(2-(2-thienyl)vinyl)-1H-pyrazol-1-yl]methanone stimulation of $^3$H-thymidine incorporation was inhibited by 75%. Although Applicants are not bound by theory, this study also demonstrates that (4-chlorophenyl)[3-(2-(2-thienyl)vinyl)-1H-pyrazol-1-yl]methanone promotes proliferation of HUVECs via the c-met receptor. In another related experiment, (4-chlorophenyl)[3-(2-(2-thienyl)vinyl)-1H-pyrazol-1-yl] methanone (12 microgram/ml) was incubated with the initial target molecule C-met receptor (5 microgram/ml) for 30 min and then added to the cells. Compound-induced EC proliferation was blocked by 40% in the presence of C-met receptor.

EXAMPLE 4

Figure 2A:
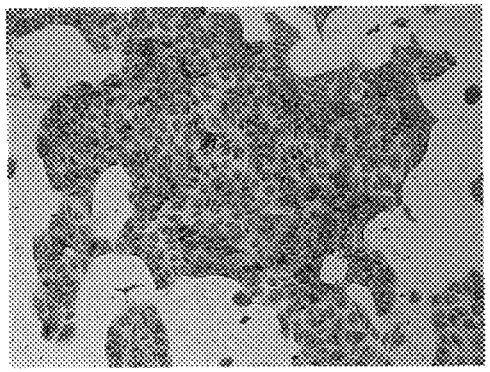
FIGS. 2A–B show the induction of scatter of MDCK cells by (4-chlorophenyl)[3-(2-(2-thienyl)vinyl)-1H-pyrazol-1-yl]methanone.
Figure 2B:
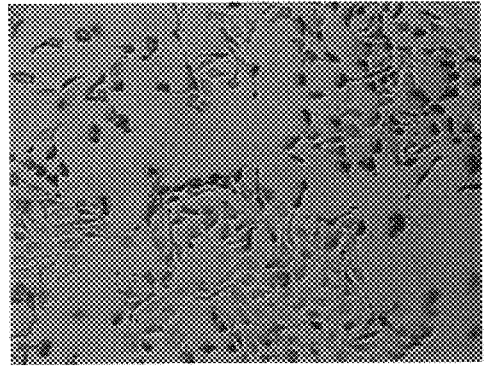

Scatter of MDCK Cells (4-chlorophenyl)[3-(2-(2-thienyl)vinyl)-1H-pyrazol-1-yl]methanone was further tested for HGF/SF activity in a standard scatter assay which is specific for HGF/SF. The ability to scatter was demonstrated for the first time using a non-peptide candidate compound. Scatter of MDCK cells by (4-chlorophenyl)[3-(2-(2-thienyl)vinyl)-1H-pyrazol-1-yl]methanone further demonstrates that its actions are mediated through stimulation of the c-Met receptor. As shown in FIG. 2, the compound caused scattering of MDCK cells similar to that seen with HGF/SF. FIG. 2A: Control cells; FIG. 2B: (4-chlorophenyl)[3-(2-(2-thienyl)vinyl)-1H-pyrazol-1-yl]methanone, 6 microgram/ml.

EXAMPLE 5

Figure 3:
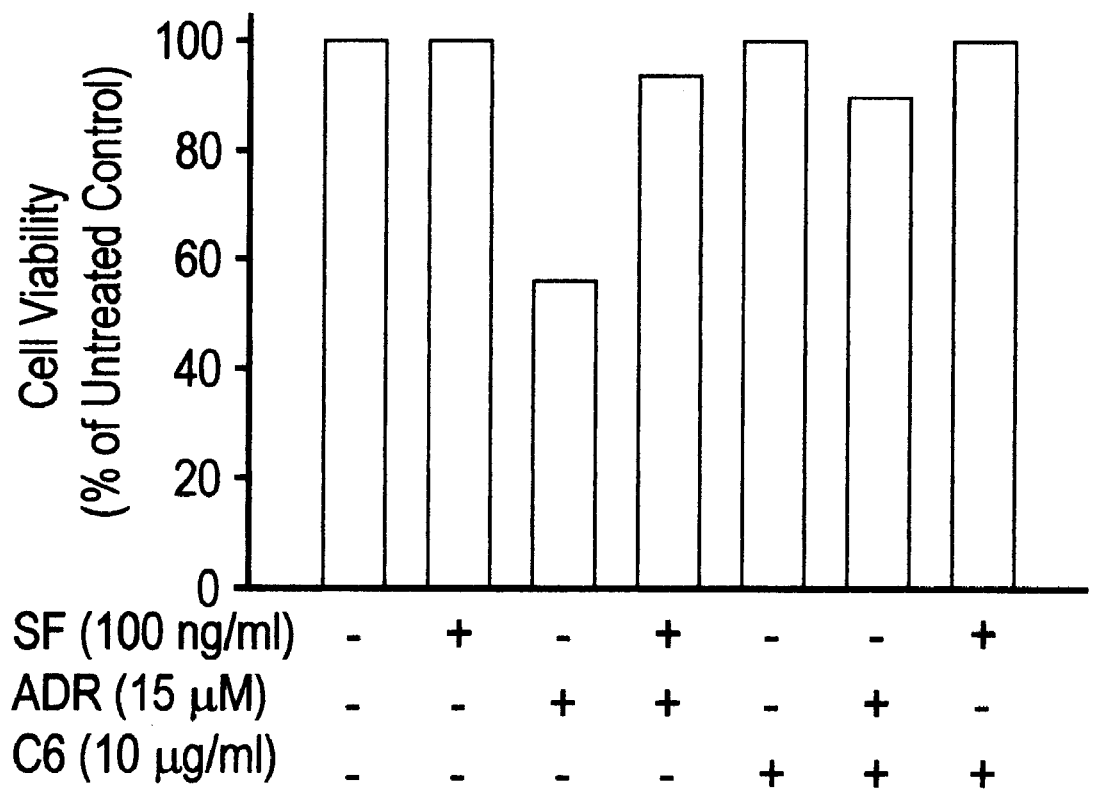
FIG. 3 shows the protection of MDCK cells from adriamycin-induced apoptosis by (4-chlorophenyl)[3-(2-(2-thienyl)vinyl)-1H-pyrazol-1-yl]methanone.

Anti-Apoptotic Activity of (4-chlorophenyl)[3-(2-(2-thienyl)vinyl)-1H-pyrazol-1-yl]methanone HGF/SF has significant anti-apoptotic activity in a number of cultured cell lines. Using the MTT cell viability assay the ability of (4-chlorophenyl)[3-(2-(2-thienyl)vinyl)-1H-pyrazol-1-yl]methanone to protect cells from adriamycin-induced apoptosis was evaluated. Like HGF/SF, (4-chlorophenyl)[3-(2-(2-thienyl)vinyl)-1H-pyrazol-1-yl] methanone was able to significantly block adriamycin-induced apoptosis in MDCK cells (FIG. 3). Cell viability was unchanged by either HGF/SF alone (column 2), (4-chlorophenyl)[3-(2-(2-thienyl)vinyl)-1H-pyrazol-1-yl] methanone alone (column 5) or HGF/SF and (4-chlorophenyl)[3-(2-(2-thienyl)vinyl)-1H-pyrazol-1-yl] methanone combined (column 7). Adriamycin (15 mM) decreased cell viability to 56% of control (column 3). Treatment with either HGF/SF (column 4) or (4-chlorophenyl)[3-(2-(2-thienyl)vinyl)-1H-pyrazol-1-yl] methanone (column 6) effected nearly complete (94%) protection from adriamycin-induced apoptosis.

In another cell line, 90% protection was afforded by (4-chlorophenyl)[3-(2-(2-thienyl)vinyl)-1H-pyrazol-1-yl] methanone.

EXAMPLE 6

Figure 4:
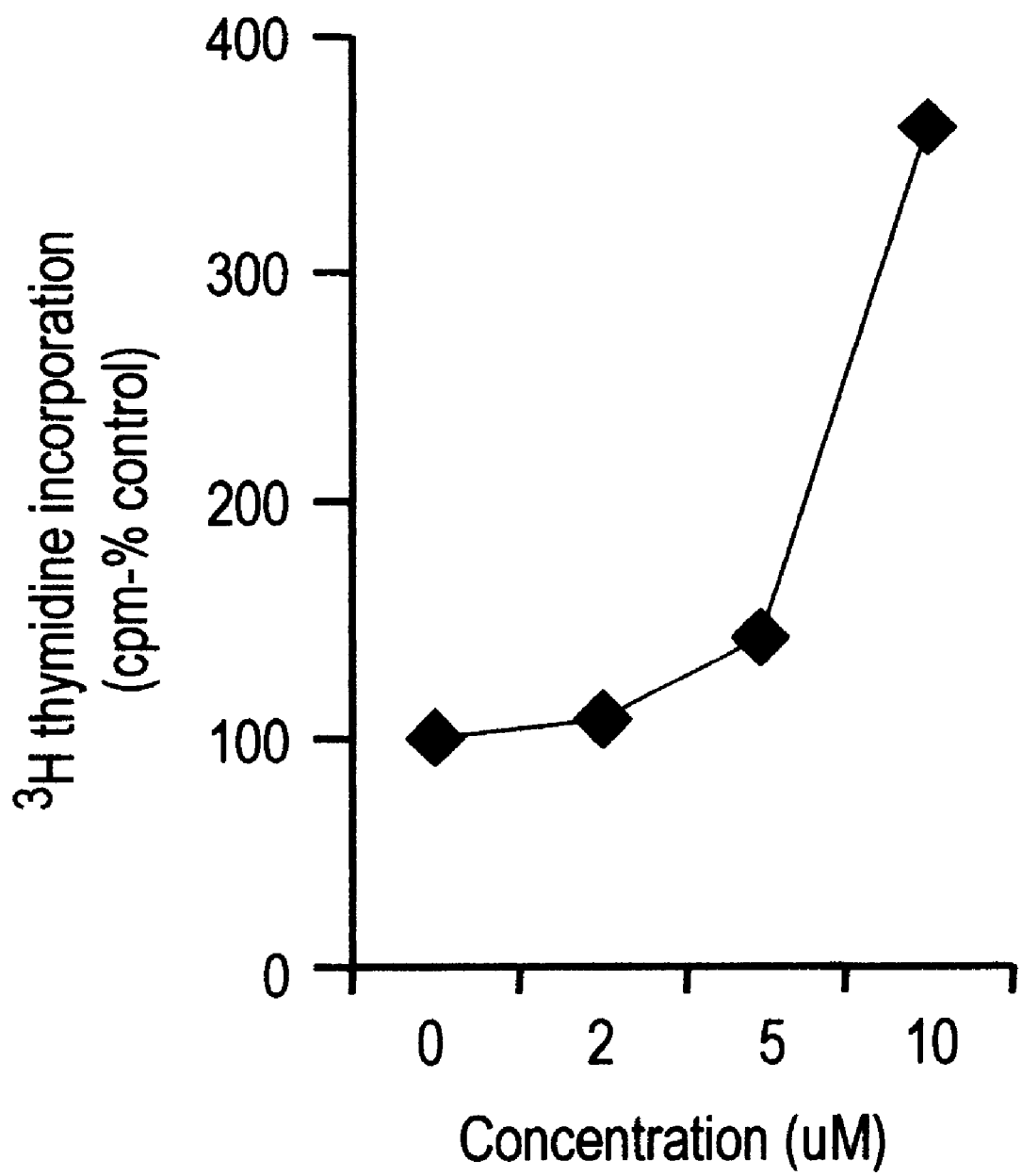
FIG. 4 shows a dose-response curve of the stimulation of endothelial cell proliferation by (4-chlorophenyl)[3-(2-(2-thienyl)vinyl)-1H-pyrazol-1-yl]methanone.

Effect of (4-chlorophenyl)(5-2-(2-thienyl)vinyl)-1H-pyrazol-1-yl-methanone on HUVEC Proliferation FIG. 4 shows a dose-response relationship between the level of level (4-chlorophenyl)(3-2-(2-thienyl)vinyl)-1H-pyrazol-1-yl-methanone and HUVEC proliferation.

EXAMPLE 7

Gene Expression

Preliminary GeneChip studies using the compounds of the invention demonstrate similar gene stimulation profiles including stimulation of interleukin-8 and angiopoetin-2, both of which have important roles in the angiogenic cascade.

EXAMPLE 8

Figure 5:
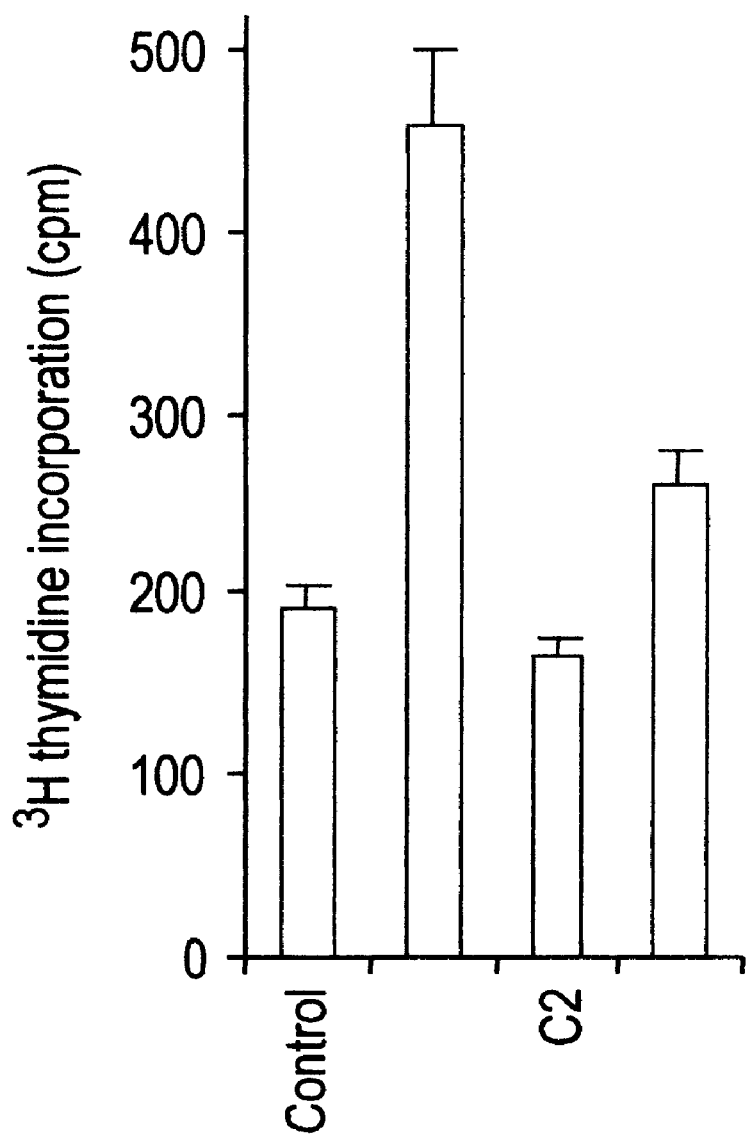
FIG. 5 shows the ability of the compound 4-(2,6-dichlorobenzyl)-3,5-dimethyl-1H-pyrazol-1-yl)-3-(2,6-dichlorophenyl)-5-methanone on HGF/SF-mediated endothelial cell proliferation.

Effect of [4-(2,6-dichlorobenzyl)-3,5-dimethyl-1H-pyrazol-1-yl][3-(2,6-dichlorophenyl)-5-methylisoxazol-4-yl]methanone on HGF/SF-Mediated HUVEC Proliferation FIG. 5 shows the results of a HUVEC growth experiment in the presence of HGF/SF and [4-(2,6-dichlorobenzyl)-3,5-dimethyl-1H-pyrazol-1-yl][3-(2,6-dichlorophenyl)-5-methylisoxazol-4-yl]methanone. While the addition of HGF/SF increases the proliferation of HUVEC (second bar), and the compound alone has no effect on baseline proliferation, the combination of both HGF/SF and the compound (fourth bar) results in significant suppression of HGF/SF-mediated stimulation.

EXAMPLE 9

In Vivo Blood Vessel Ingrowth Assay

Angiogenesis was assayed as growth of blood vessels from subcutaneous tissue into a solid gel of basement membrane containing the test compound. Matrigel in liquid form (0.5 ml) was mixed with a compound of the invention, or basic fibroblast growth factor as a control, and injected into the abdominal subcutaneous tissue of mice as previously described (Kibbey, M. C., Grant, D. S. Auerbach, R. and Kleinman, H. K. [1992] Role of the SIKVAV site of laminin in promotion of angiogenesis and tumor growth: an in vivo Matrigel model. J. Natl. Can. Inst. 84, 1633–38). After 10 days, mice were sacrificed and the Matrigel plugs were removed, fixed, sectioned, stained and examined for ingrowth of blood vessels. In FIG. 6A, the effect of 1-(4-chloro-3-methylphenyl)-3-(2,6-dichlorophenyl)-prop-2-en-1-one was seen as a nearly complete inhibition of blood vessel ingrowth, less than control. In contrast, in FIG. 6B, (4-(2-chloro-6-fluorobenzyl)-3,5-dimethyl-1H-pyrazol-1-yl)(3-(2,6-dichlorophenyl)-5-methylisoxazol-4-yl) methanone showed significant stimulation of blood vessel ingrowth.

EXAMPLE 10

Clonogenic Assays

Figure 7:
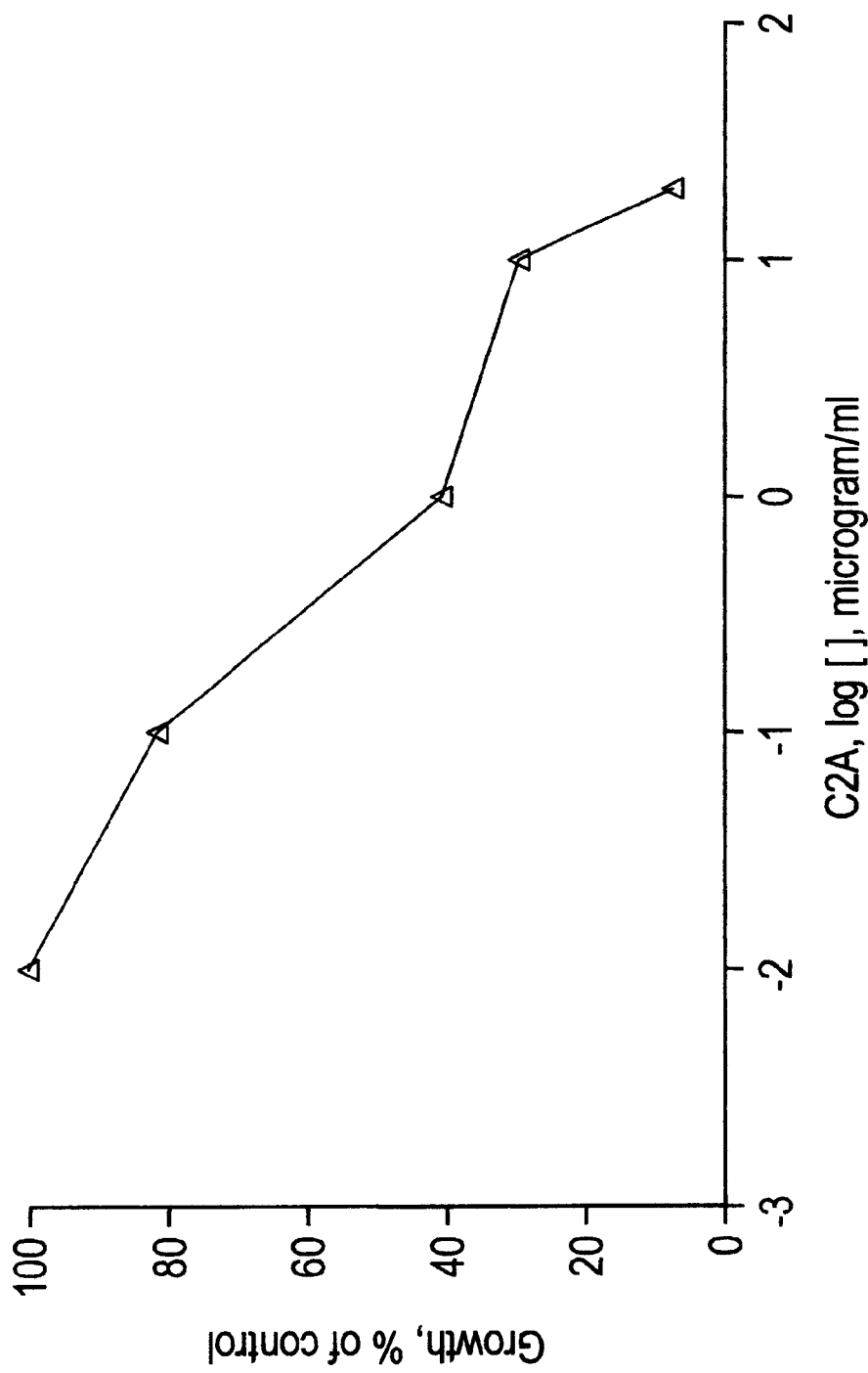
FIG. 7 shows the results of a clonogenic assay using DU145 cells and (4-(2-chloro-6-fluorobenzyl)-3,5-dimethyl-1H-pyrazole-1-yl)(3-(2,6-dichlorophenyl)-5-methylisoxazol-4-yl) methanone.
Figure 8:
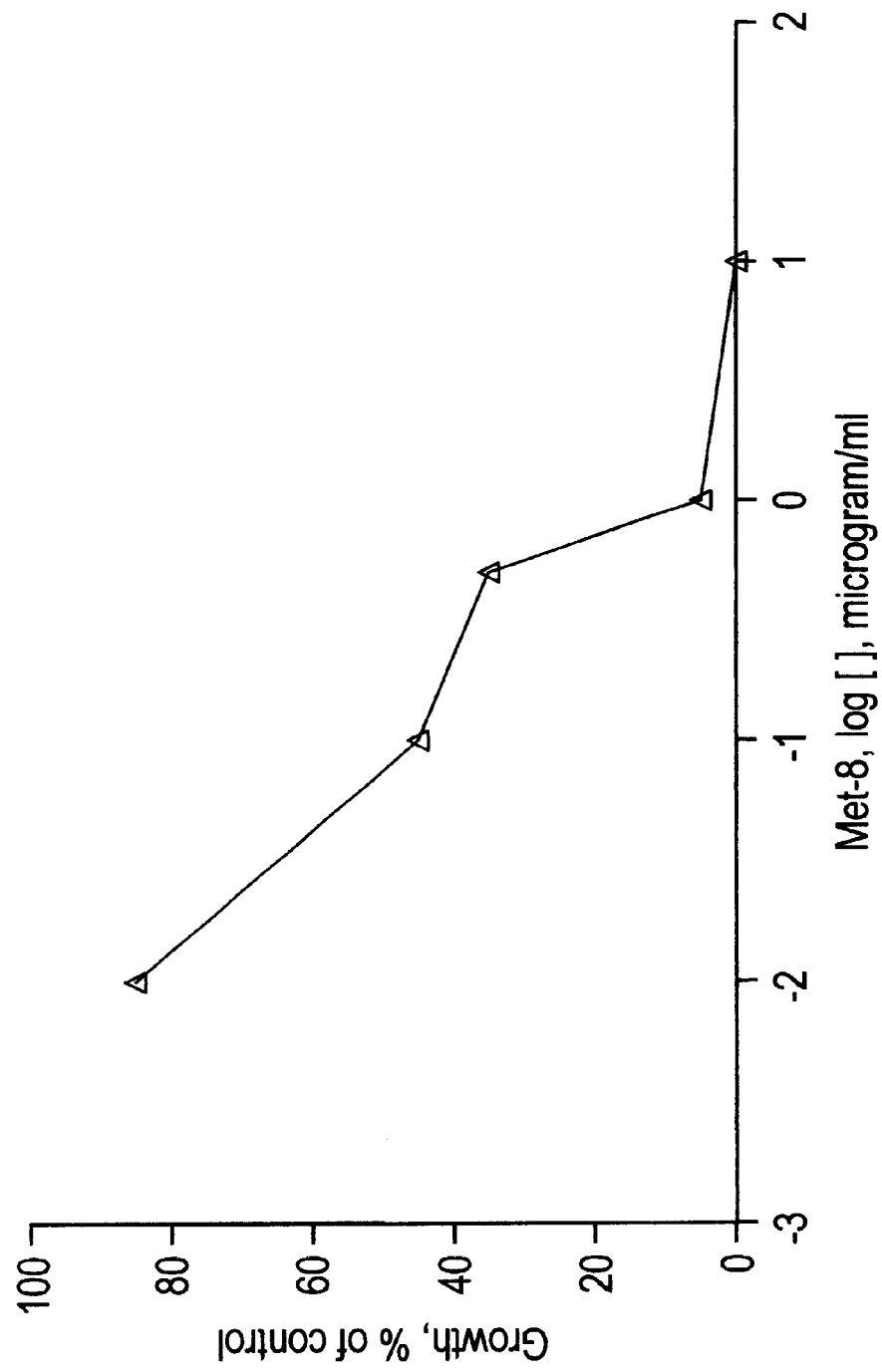
FIG. 8 shows the results of a clonogenic assay using DU145 cells and 1-(4-chloro-3-methylphenyl)-3-(2,6-dichlorophenyl)-prop-2-en-1-one.

The effect of (4-(2-chloro-6-fluorobenzyl)-3,5-dimethyl-1H-pyrazole-1-yl)(3-(2,6-dichlorophenyl)-5-methylisoxazol-4-yl)methanone (FIG. 7) and 1-(4-chloro-3-methylphenyl)-3-(2,6-dichlorophenyl)-prop-2-en-1-one were evaluated in a clonogenic assay over 7 days. Both FIGS. 7 and 8 show dose responsive inhibition of DU145 cell growth during the experiment.

EXAMPLE 11

In Vivo Blood Flow Improvement Assay

Figure 9:
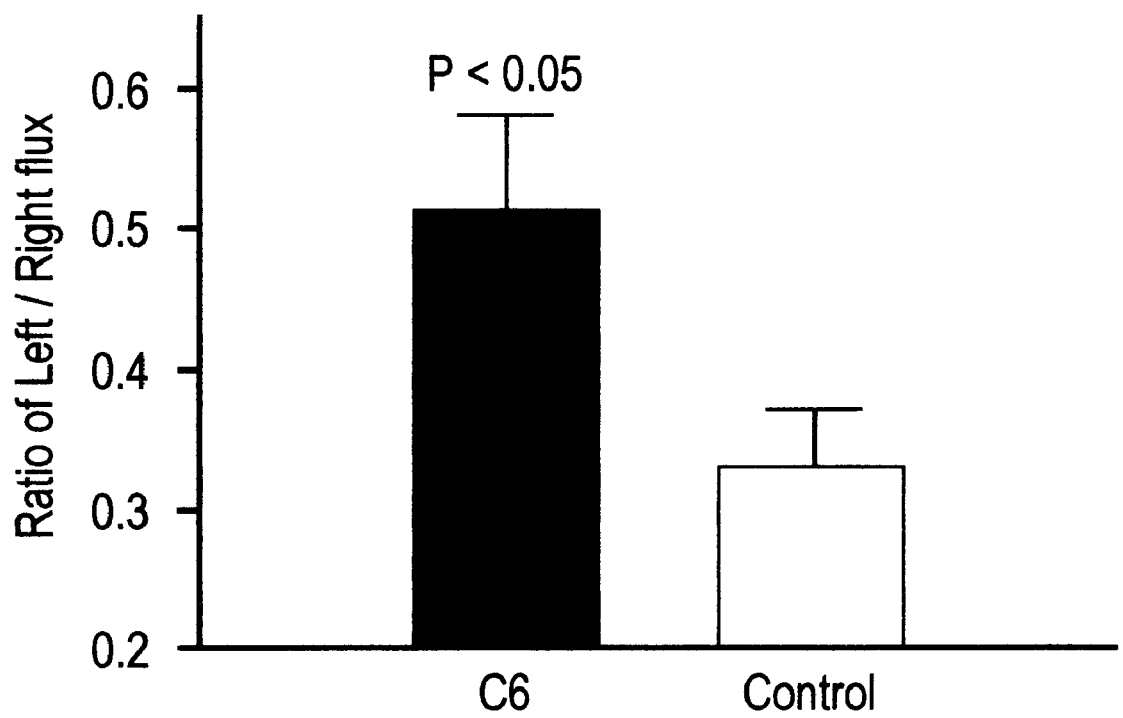
FIG. 9 shows improved blood flow in mice following removal of the femoral artery after treatment with (4-chlorophenyl)[3-(2-(2-thienyl)vinyl)-1H-pyrazol-1-yl] methanone.

FIG. 9 shows the results of an in-vivo experiment in which (4-chlorophenyl)[3-(2-(2-thienyl)vinyl)-1H-pyrazol-1-yl]methanone was administered to mice for seven days following removal of the femoral artery. The results show significant improvement in blood flow with the compound.

EXAMPLE 11

Other Compounds with Activities

In a similar manner as described above, the following compounds related were evaluated for stimulation of endothelial cell proliferation. Three different rounds of testing were performed.

| Compound | Stimulation/ Inhibition at 5 microg/ml | Stimulation/ Inhibition at 10 microg/ml |
|---|---|---|
| 1-(methylsulfonyl)-3-(2-(2-thienyl)vinyl)-1H-pyrazole | 74% stimulation | Not significant |
| 2,2-dimethyl-1-(3-(2-(2-thienyl)vinyl)-1H-pyrazole-1-yl)propan-1-one | No effect | 55% stimulation |
| N-methyl-3-(2-(2-thienyl)vinyl)-1H-pyrazole-1-carboxamide | 70% stimulation | 42% stimulation |
| (4-chlorophenyl)(3-(3-phenylisoxazol-5-yl)-1H-pyrazol-1-yl)methanone | 54% stimulation | 60% stimulation |
| (4-chlorophenyl)(3-(5-(2-thienyl)-2-thienyl)-1H-pyrazol-1-yl)methanone | 40% stimulation | 40% stimulation |
| (4-(2-chloro-6-fluorobenzyl)-3,5-dimethyl-1H-pyrazol-1-yl)(4-chlorophenyl)methanone | 41% stimulation | 35% stimulation |
| (4-chlorophenyl)(5-(methylthio)-3-(4-phenoxyphenyl)-1H-pyrazol-1-yl)methanone | No effect | 40% inhibition |
| (4-chlorophenyl)(3,5-dimethyl-4-((1-methyl-1H-imidazol-2-yl)thio)-1H-pyrazol-1-yl)methanone | 52% stimulation | 50% stimulation |
| N1-phenyl-3-(2-(2-thienyl)vinyl)-1H-pyrazole-1-carboxamide | 40% stimulation | Not significant |
| (4-chlorophenyl)(3-(2-(5-(2-thienyl)-2-thienyl)-4-methyl-1,3-thiazol-5-yl)-1H-pyrazol-1-yl)methanone | 20% stimulation | 33% stimulation |
| (3-benzhydryl-1H-pyrazol-1-yl)(4-chlorophenyl)methanone | No effect | 25% stimulation |
| N1-(4-chlorophenyl)-3-(2-(2-thienyl)vinyl)-1H-pyrazole-1-carboxamide | No effect | 55% stimulation |
| methyl 1-(4-chlorobenzoyl)-5-isoxazol-5-yl-3-methyl-1H-pyrazole-4-carboxylate | Not significant | 33% stimulation |
| 2-chloro-6-(4-(1-(4-chlorobenzyl)-1H-pyrazol-5-yl)phenoxy)benzonitrile | 60% stimulation | 90% stimulation |

The following compounds were re-evaluated.

| Compound | Stimulation/ Inhibition at 5 microg/ml | Stimulation/ Inhibition at 10 microg/ml |
|---|---|---|
| 4(5-chlorobenzo(b)thiophen-3-yl)-1-(2-chlorophenyl)sulfonyl)-3,5dimethyl-1-H-pyrazole | 1.8 fold stimulation | Not significant |

| Compound | Stimulation/Inhibition at 5 microg/ml | Stimulation/Inhibition at 10 microg/ml |
|---|---|---|
| 4-(2,6-dichlorobenzyl)-3-methyl-1-phenyl-1H-pyrazol-5-ol | 2.3 fold stimulation | two fold stimulation |
| 3-methyl-4-(2-methylallyl)-1-(phenylsulfonyl)-1H-pyrazol-5-ol | two fold stimulation | Not significant |
| [3-(2,6-difluorophenyl)-4-ethyl-1H-pyrazol-1-yl](2-thienyl)methanone | 2.5 fold stimulation | two fold stimulation |
| 4-[(5-chloro-1-benzothiophen-3-yl)methyl]-N,3,5-trimethyl-1H-pyrazole-1-carboxamide | two fold stimulation | two fold stimulation |
| 3-(2,6-difluorophenyl)-4-ethyl-1H-pyrazole | two fold stimulation | 86% stimulation |
| N1-(3-chlorophenyl)-4-[(5-chlorobenzo[b]thiophen-3-yl)methyl]-3,5-dimethyl-1H-pyrazole-1-carboxamide | 86% stimulation | 40% stimulation |
| {4-[(5-chlorobenzo[b]thiophen-3-yl)methyl]-3,5-dimethyl-1H-pyrazol-1-yl}(4-nitrophenyl)methanone | 74% stimulation | 2.5 fold stimulation |
| N1-phenyl-4-[(5-chlorobenzo[b]thiophen-3-yl)methyl]-3,5-dimethyl-1H-pyrazole-1-carboxamide | two fold stimulation | 45% stimulation |
| 4-[(5-chloro-1-benzothiophen-3-yl)methyl]-N-(2,4-dichlorophenyl)-3,5-dimethyl-1H-pyrazole-1-carboxamide | 75% stimulation | 35% stimulation |
| 1-[3-(2,6-difluorophenyl)-4-ethyl-1H-pyrazol-1-yl]-2,2-dimethylpropan-1-one | 58% stimulation | not significant |
| 4-(2-chloro-6-fluorobenzyl)-1-{[3,5-di(trifluoromethyl)phenyl]sulfonyl}-3,5-dimethyl-1H-pyrarole | 3.1 fold stimulation | 2.4 fold stimulation |

EXAMPLE 12

Inhibitors of Cellular Proliferation

[4-(2,6-dichlorobenzyl)-3,5-dimethyl-1H-pyrazol-1-yl][3-(2,6-dichlorophenyl)-5methylisoxazol-4-yl]methanone was evaluated for the ability to block HGF/SF induced proliferation of HUVEC as described above. It demonstrated 40–60% blockage at 12 micrograms/ml.

EXAMPLE 13

Inhibition of Tumor Growth

[4-(2,6-Dichlorobenzyl)-3,5-dimethyl-1H-pyrazol-1-yl][3-(2,6-dichlorophenyl)-5-methylisoxazol-4-yl]methanone was evaluated for inhibition of human endometrial cancer tumor growth. Growth was inhibited by 40–50% at 40 micrograms/ml.

EXAMPLE 14

Anti-Proliferative Activity of Compounds of the Invention

Using the above-described assays, the following compounds were found to block proliferation of HUVEC in the absence or presence of exogenously-added HGF/SF.

| Compound | Activity at 2 microgram/ml | | Activity at 6 microgram/ml | |
|---|---|---|---|---|
| | Without HGF/SF | With HGF/SF | Without HGF/SF | With HGF/SF |
| (4-(2-chloro-6-fluorobenzyl)-3,5-dimethyl-1H-pyrazole-1-yl)(3-(2,6-dichlorophenyl)-5-methylisoxazol-4-yl)methanone | No effect | 40–90% inhibition | not significant | 50–100% inhibition |
| 4-(2-chloro-6-fluorobenzyl)-1-((3,4-dichlorophenyl)sulfonyl)-3,5-dimethyl-1H-pyrazole | 73% stimulation | not significant | not significant | not significant |
| 4-(2-chloro-6-fluorobenzyl)-1,3,5-trimethyl-1H-pyrazole | 50% stimulation | No effect | No effect | blocked SF by 30% |
| 4-(2-chloro-6-fluorobenzyl)-3,5-dimethyl-1H-pyrazole | 54% stimulation | No effect | No effect | No effect |
| (4-bromo-3,5-dimethyl-1H-pyrazol-1-yl)(3-(2,6-dichlorophenyl)isoxazole-4-carbohydrazide) | 74% stimulation | No effect | Not significant | No effect |
| N'4,5-dimethyl-N'4-(5-nitro-2-pyridyl)-3-(2,6-dichlorophenyl)isoxazole-4-carbohydrazide | No effect | No effect | No effect | blocked SF by 43% |
| N'4-(2-(((2,4-dichlorobenzylidene)amino)oxy)acetyl)-3-(2,6-dichlorophenyl)-5-methylisoxazole-4-carbohydrazide | 32% stimulation | 30% stimulation | No effect | No effect |
| 3-(2,6-dichlorophenyl)-5-methylisoxazole-4-carbohydrazide | not significant | not significant | not significant | not significant |
| N'4-(3-(3,4,5-trimethoxyphenyl)propanoyl)-3-(2,6-dichlorophenyl)-5-methylisoxazole-4-carbohydrazide | 50% inhibition | Blocked SF by 50% | Cytotoxic | |
| 2-nitrophenyl 2-((3-(2,6-dichlorophenyl)-5-methylisoxazol-4-yl)carbonyl)hydrazine-1-carbothioate | No effect | No effect | 80% inhibition | 80% inhibition |
| 1-((4-chlorophenyl)sulfonyl)-4-(2,6-dichlorobenzyl)-3,5-dimethyl-1H-pyrazol | No effect | No effect | No effect | 50% inhibition |
| 3-(4-(2,6-dichlorobenzyl)-3,5-dimethyl-1H-pyrazol-1-yl)propanenitrile | No effect | 36% inhibition | 34% inhibition | 65% inhibition |
| N'4-((2-methyl-1,3-thiazol-4-yl)carbonyl)-3-(2,6-dichlorophenyl)-5-methylisoxazole-4-4carbohydrazide | No effect | 50% inhibition | 52% stimulation | 50% inhibition |
| N1-((2-(3-(2,6-dichlorophenyl)-5-methylisoxazol-4-yl)carbonyl) | No effect | No effect | No effect | 25% inhibition |

-continued

| Compound | Activity at 2 microgram/ml | | Activity at 6 microgram/ml | |
|---|---|---|---|---|
| | Without HGF/SF | With HGF/SF | Without HGF/SF | With HGF/SF |
| hydrazino)(methylthio)methylidene)benzene-1-sulfonamide | | | | |
| N'4-(2,4,6-trichloro-phenyl)-3-3(2,6-dichlorophenyl)-5-methylisoxazole-4-carbohydrazide | No effect | No effect | No effect | 60% inhibition |
| N'4,3-di(2,6-dichloro-phenyl)-5-methyli-soxazole-4-carbohydra-zide | No effect | not significant | 30% inhibition | 60% inhibition |
| 3,5-di(tert-butyl)-4-(2-chloro-6-fluoro-benzyl)-1H-pyrazole | 51% stimulation | 25% inhibition | No effect | 50% inhibition |
| N'4-(3,5-dichloro-4-pyridyl)-3-(2,6-dichlorophenyl)-5-methylisoxazole-4-carbohydrazide | No effect | 25% inhibition | No effect | 25% inhibition |
| N'4-phenyl-3-(2,6-dichlorophenyl)-5-methylisoxazole-4-carbohydrazide | No effect | 40% inhibition | No effect | 80% inhibition |
| (4-(2-chloro-6-fluorobenzyl)-3,5-dimethyl-1H-pyrazole-1-yl)(2,6-dichloro-phenyl)methanone | not significant | 23% inhibition | not significant | 90% inhibition |
| 1-(4-(2-chloro-6-fluorobenzyl)-3,5-dimethyl-1H-pyrazole-1-yl)2,2-dimethyl-propan-1-one | No effect | 25% inhibition | No effect | 25% inhibition |
| N'4,N'4,5-trimethyl-3-(2,6-dichloro-phenyl)isoxazole-4-carbohydrazide | No effect | No effect | No effect | 40% inhibition |
| N4-azepan-1-yl-3-(2,6-dichlorophenyl)-5-methylisoxazole-4-carboxamide | No effect | No effect | 50% inhibition | 50% inhibition |
| N'4-(6-(trifluoromethyl)-2-pyridyl)-3-(2,6-dichlorophenyl)-5-methylisoxazole-4-carbohydrazide | 40% inhibition | 50% inhibition | 50% inhibition | 80% inhibition |
| (4-(2-chloro-6-fluorobenzyl)-3,5-dimethyl-1H-pyrazole-1-yl)(4-chlorophenyl)methanone | 40% stimulation | blocked SF by 30% | 50% inhibition | 90% inhibition |
| N'4-(3,3-diethoxy-propanoyl)-3-(2,6-dichlorophenyl)-5-methylisoxazole-4-carbohydrazide | No effect | No effect | No effect | 35% inhibition |
| (4-(2-chloro-6-fluoro-benzyl)-3,5-dimethyl-1H-pyrazole-1-yl)(2-thienyl)methanone | No effect | No effect | No effect | 61% inhibition |

EXAMPLE 14

Activities of Other Compounds

The following compounds, structurally unrelated to those described in the foregoing examples, were also evaluated for effects on endothelial cell proliferation in the absence and presence of exogenously-added HGF/SF. Several compounds with potential antiproliferative activity showed activity, including those which showed activity only in the presence of exogenous HGF/SF. Moreover, several compounds demonstrated stimulatory activity, and have potential growth promoting activities useful as described hereinabove.

| Compound | Stimulation/Inhibition at 6–12 micrograms/ml | |
|---|---|---|
| | Without HGF/SF | With |
| tetraphenylthiophene | 50% inhibition | No effect |
| pentaphenylbenzene | two to three fold stimulation | 50% inhibition |
| 1,3,5-triphenylbenzene | 40–60% stimulation | two fold stimulation |
| (3-Biphenyl) Trimethyl silane | 40% stimulation | No effect |
| 16 methyl-16 Dehydropregnenolone | No effect | 30% stimulation |
| 9-biphenyl-4-ylmethylene-9H-tri-benzo(A,C,E)-cycloheptene | 30–40% stimulation | 20–30% stimulation |
| 1,1,3-triphenylinedene | 50–100% stimulation | 30–40% stimulation |
| 9,9-Biphenanthrene | No effect | 20–40% inhibition |
| N-(furfurylidene)-2,4-xylidine | 30–40% inhibition | 50–60% inhibition |
| 1-(4-Chloro-3 Methyl Phenyl)3-2(2,6-dichlorophenyl)Prop-2-ene-1-one | No effect at 1 ug/ml | 40–80% inhibition |
| 3-(4-Bromophenyl)-1-phenylprop-2-en-1-one | 40–80% stimulation at 1 ug/ml | some additive effect |

| | Activity at 1 ug/ml concentration | |
|---|---|---|
| | Without HGF/SF | With HGF/SF |
| 8-Benzyledene-2,4 Diphenyl-5,6,7,8 Tetrahydrophosphinoline | no significant effect | 40% inhibition |
| 6-(3,5-Dimethylphenyl) Thio)-3-Phenyl (1,2,4-Triazolo(4,3-b)pyridazine | no significant effect | 30% inhibition |

EXAMPLE 15

Inhibition of HGF/SF, VEGF and FGF Activities

Figure 10B:
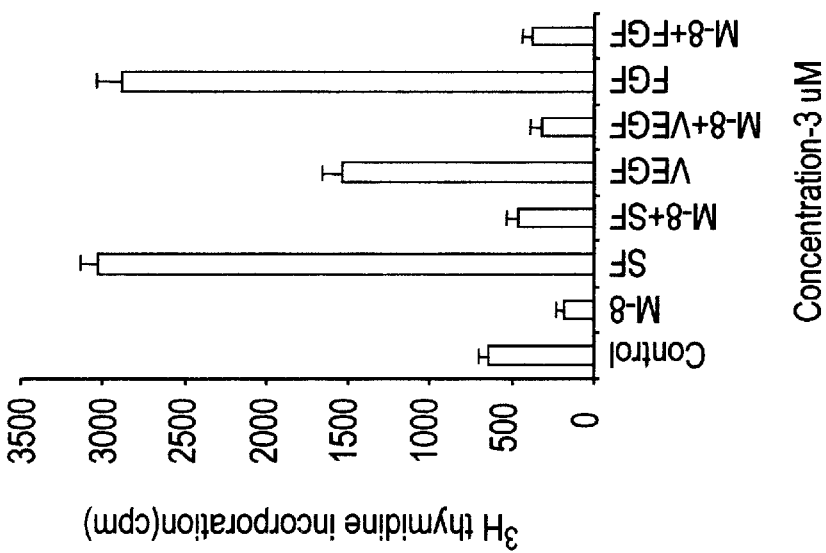
FIGS. 10A–B shows the effect of the compound 1-(4-chloro-3-methylphenyl)-3-(2,6-dichlorophenyl)-prop-2-en-1-one on inhibition of endothelial cell proliferation induced by the growth factors HGF/SF, VEGF and FGF at 1.5 micromolar (A) and 3.0 micromolar (B).
Figure 10A:
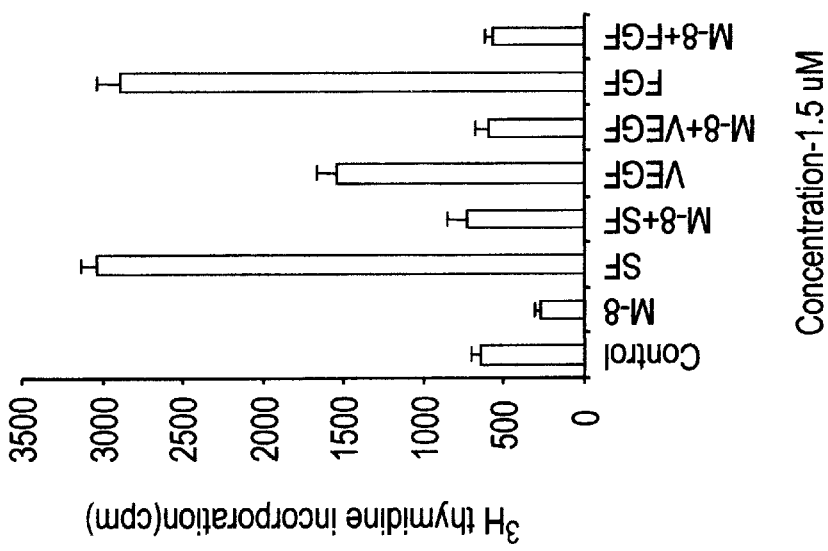

In endothelial cell proliferation assays as described above, the effect of the compound 1-(4-chloro-3-methylphenyl)-3-(2,6-dichlorophenyl)-prop-2-en-1-one was evaluated in the presence of HGF/SF, VEGF or FGF for its effects on antagonizing the growth factor-induced stimulation of endothelial cell proliferation. As shown in FIG. 10A, at 1.5 micromolar, the compound suppressed the HGF/SF-, VEFG- and FGF-mediated increase in endothelial cell proliferation. Similar results were seen with 3 micromolar 1-(4-chloro-3-methylphenyl)-3-(2,6-dichlorophenyl)-prop-2-en-1-one, FIG. 10B.

EXAMPLE 16

Compounds with VEGF-Like Activity

Figure 11:
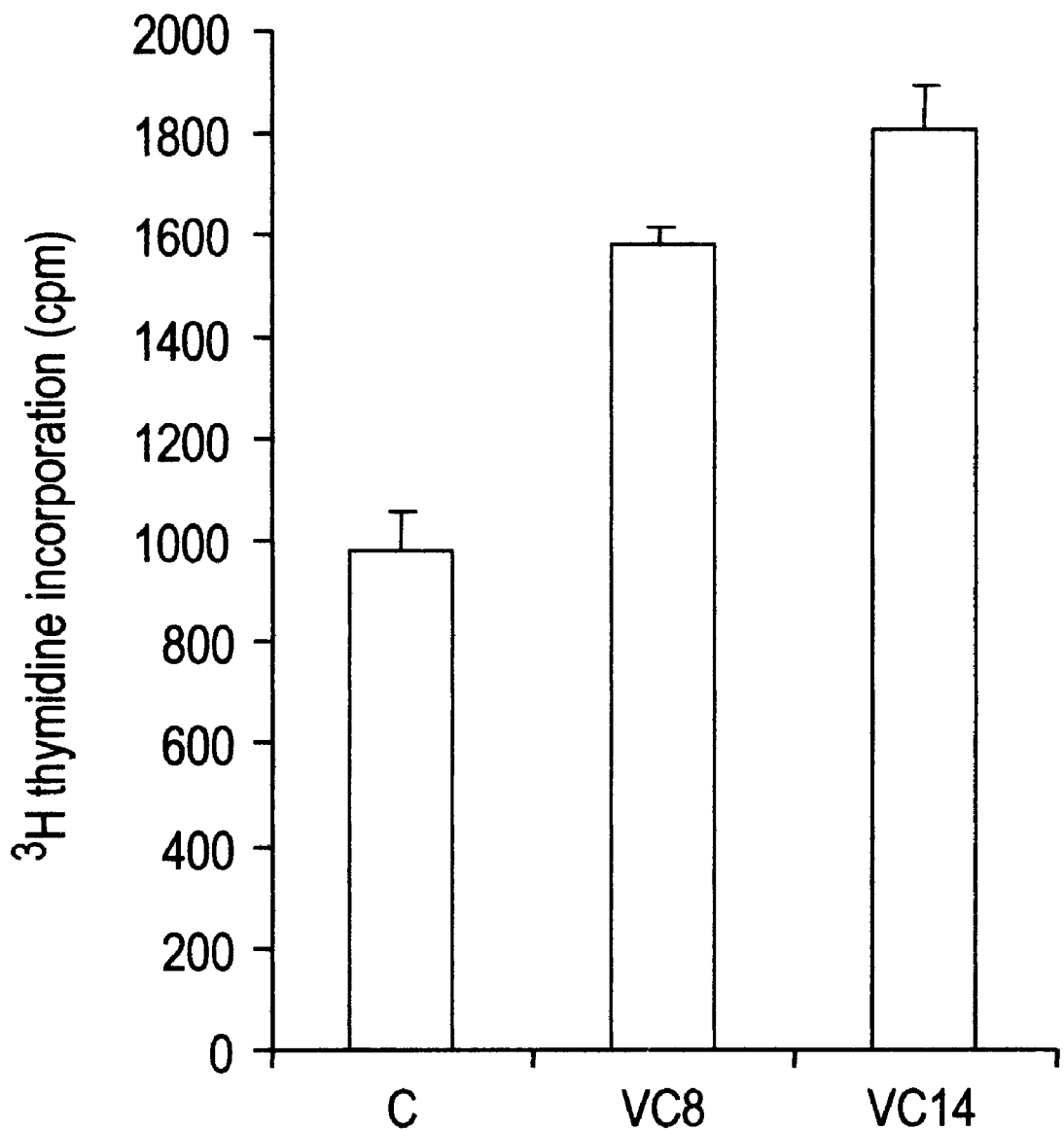
FIG. 11 shows the VEGF-like activity of two compounds of the invention.

Compounds were screened for VEGF-like activity in a standard assay using 2 microgram/ml compound. As shown in FIG. 11, 3,3-dibromo-1-phenyl-1,2,3,4-tetrahydroquinoline-2,4-dione (VC8) and 4-(4-chlorophenyl)-6-(dimethylamino)-2-phenyl-5-pyrimidinecarbonitrile (VC14) showed positive activity, both of which were better than VEGF (1259±104 cpm). The present invention is also directed to methods of use of these and structurally-related VEGF agonists or mimics for the treatment of various conditions and diseases for which VEGF would be useful for therapy in a mammal, preferably a human, such as but not limited to acceleration of wound healing, and in particular, diabetic wound healing. The compounds are generally useful for promoting proliferation of vascular endothelial cells and promoting vascularization, for such other uses as restenosis for treatment of coronary artery disease, angina and other ischemic diseases, including stroke.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

Matsumoto, K, and Nakamura, T. (1997) Hepatocyte growth factor (HGF) as a tissue organizer for organogenesis and regeneration. Biochem. Biophys. Res. Commun. 239, 639–44

Boros, P. and Miller, C. M. (1995) Hepatocyte growth factor: a multifuinctional cytokine. Lancet 345, 293–5.

Morislhita, R, Nakamura, S, Nakamnura, Y, Aoki, M, Moriguchi, A, Kida, I, Yo, Y, Matsumoto, K, Nakamura, T, Higaki, J, Ogihara, T (1997) Potential role of an endothelium-specific growth factor, hepatocyte growth factor, on endothelial damage in diabetes. Diabetes 46:138–42.

Grant, D. S, Kleinman, H. K., Goldberg, I. D., Bhargava, M. M., Nickoloff, B. J., Kinsella, J. L., Polverini, P., Rosen, E. M. (1993) Scatter factor induces blood vessel formation in vivo. Proc. Natl. Acad. Sci. USA 90:1937–41.

Morishita, R., Nakamura, S., Hayashi, S., Taniyama, Y., Moriguchi, A., Nagano, T., Taiji, M., Noguchi, H., Takeshita, S., Matsumoto, K., Nakamura, T., Higaki, J., Ogihara, T. (1999) Therapeutic angiogenesis induced by human recombinant hepatocyte growth factor in rabbit hind limb ischemia model as cytokine supplement therapy. Hypertension 33:1379–84.

Jeffers, M., Rong, S., Woude, G. F. (1996) Hepatocyte growth factor/scatter factor-Met signaling in tumorigenicity and invasion/metastasis. J. Mol. Med. 74:505–13.

Moriyama, T., Kataoka, H., Koono, M., Wakisaka, S. (1999) Expression of hepatocyte growth factor/scatter factor and its receptor c-Met in brain tumors: evidence for a role in progression of astrocytic tumors Int. J. Mol. Med. 3:531–6.

Gherardi, E., Hartmann, G., Hepple, J., Chirgadze, D., Srinivasan, N., Blundell, T. (1997) Domain structure of hepatocyte growth factor/scatter factor (HGF/SF). Ciba Found Symp 212:84–93.

Naldini, L., Tamagnone, L., Vigna, E., Sachs, M., Hartmann, G., Birchmeier, W., Daikuhara, Y., Tsubouchi, H., Blasi, F., Comoglio, P.M. (1992) Extracellular proteolytic cleavage by urokinase is required for activation of hepatocyte growth factor/scatter factor. EMBO J. 11:4825–33.

Bardelli, A., Ponzetto, C., Comoglio, P.M. (1994) Identification of functional domains in the hepatocyte growth factor and its receptor by molecular engineering. *J. Biotechnol.* 37:109–22.

Sakata, H, Stahl, S. J, Taylor, W. G, Rosenberg, J. M, Sakaguchi, K, Wingfield, P. T, and Rubin, J. S. (1997) Heparin binding and oligomerization of hepatocyte growth factor/scatter factor isoforns. Heparan sulfate glycosaminoglycan requirement for Met binding and signaling. J Biol Chem 272, 9457–9463.

Lokker, N. A., Mark, M. R., Luis, E. A., Bennett, G. L., Robbins, K. A., Baker, J. B., Godowski, P. J. (1992) Structure-function analysis of hepatocyte growth factor: identification of variants that lack mitogenic activity yet retain high affinity receptor binding. *EMBO J.* 11:2503–10.

O'Neil, K. T. and Hoess, R. H. (1995) Phage Display: Protein engineering by directed evolution. Curr. Opin. Struc. Biol. 5, 443–449.

Wrighton, N. C., Farrell, F. X., Chang, R., Kashyap, A. K., Barbone, F. P., Mulcahy, L. S., Johnson, D. L., Barrett, R. W., Jolliffe, L. K. and Dower, W. J. (1996) Small peptides as potent mimetics of the protein hormone erythropoietin. Science 273, 458–461.

Widersten, M. and Mannervik, B. (1995) Glutathione S transferase with novel active sites isolated by phage display from a library of random mutants. J. Mol. Biol. 250, 115–122.

Saggio, I. And Laufer, R. (1993) Biotin binders selected from a random peptide library expressed on phage. Biochem. J. 293, 613–616.

Pasqualini R, Koivunen, E. and Ruoslahti, E. (1995) A peptide isolated from phage display libraries is a structural and functional mimic of an RGD-binding site on integrins. J Cell Biol. 130, 1189–1196.

Koivunen E, Wang, B. and Ruoslahti, E. (1994) Isolation of a highly specific ligand for the alpha 5 beta 1 integrin from a phage display library. J Cell Biol. 124, 373–380.

S. Paka, Goldberg, I. J., Choi, S. Y. Obunike, J., Saxena, U. Goldberg, I. D. and Pillarisetti, S. (1999) Perlecan mediates the anti-proliferative effect of apolipoprotein E on smooth muscle cells J. Biol. Chem. 274, 36403.

Nicosa, R. F. and Ottinetti, A. (1990) Growth of microvessels in serum-free matrix culture of rat aorta. Lab. Invest. 63: 115–122.

Kibbey, M. C., Grant, D. S. Auerbach, R. and Kleinman, H. K. (1992) Role of the SIKVAV site of laminin in promotion of angiogenesis and tumor growth: an in vivo Matrigel model. J. Natl. Can. Inst. 84, 1633–38.

van der Voort, R., Taher, T. E., Wielenga, V. J., Spaargaren, M., Prevo, R., Smit, L., David, G., Hartmann, G., Gherardi, E., Pals, S. T. (1999) Heparan sulfate-modified CD44 promotes hepatocyte growth factor/scatter factor-induced signal transduction through the receptor tyrosine kinase c-Met. J. Biol. Chem. 274, 6499–506.

Liu, S., Julian, J., Carson, D.D. (1998) A peptide sequence of heparin/heparan sulfate (HP/HS)-interacting protein supports selective, high affinity binding of HP/HS and cell attachment. J. Biol. Chem. 273, 9718–26.

What is claimed is:

1. A method for modulating HGF/SF activity in a mammal comprising administering to said mammal an effective HGF/SF activity modulating amount of a compound with the general formula IV:

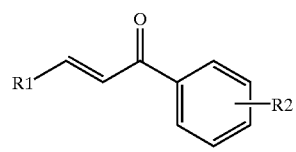

wherein
R1 is a phenyl group substituted with hydrogen, a halogen, C1 to C4 alkyl, or C1 to C4 alkyloxy, or is a heteroaryl group selected from the group consisting of 4-bromo-2-thienyl, 4-pyridyl, 2-furyl, 3-thienyl, optionally substituted with halogens and/or C1 to C4 alkyl; and R2 is one or more hydrogen, C1 to C4 alkyl, halogen, or C1 to C4 alkyloxy groups.

2. A method for modulating HGF/SF activity in a mammal comprising administering to said mammal an effective HGF/SF activity modulating amount of a compound selected from the group consisting of 1-(4-chloro-3-methylphenyl)-3-(2,6-dichlorophenyl)-prop-2-en-1-one 1-(4-chloro-3-methylphenyl)-3-(2-chlorophenyl)prop-2-en-1-one 3-(2-chloro-6-fluorophenyl)-1-(4-chloro-3-methylphenyl)prop-2-en-1-one 3-(4-bromo-2-thienyl)-1-(3,4-dichlorophenyl)prop-2-en-1-one 3-(4-bromo-2-thienyl)-1-(4-chloro-3-methylphenyl)prop-2-en-1-one 3-(4-bromo-2-thienyl)-1-(4-fluorophenyl)prop-2-en-1-one 3-(4-bromo-2-thienyl)-1-(4-chlorophenyl)prop-2-en-1-one 1-(4-chlorophenyl)-3-(2,4-dichlorophenyl)prop-2-en-1-one 3-(1,3-benzodioxol-5-yl)-1-(4-bromophenyl)prop-2-en-1-one 3-(3-phenoxy-2-thienyl)-1-(2-thienyl)prop-2-en-1-one 3-(3-bromo-4-methoxyphenyl)-1-phenylprop-2-en-one 3-(3,4-dichlorophenyl)-1-(2-nitrophenyl)prop-2-en-1-one 1-(4-chlorophenyl)-3-(3,4-dichlorophenyl)prop-2-en-1-one 1-(4-chlorophenyl)-3-(3,5-dichloro-2-hydroxyphenyl)prop-2-en-1-one 1-(2-chlorophenyl)-3-(3,5-dichloro-2-hydroxyphenyl)prop-2-en-1-one 3-(4-chlorophenyl)-1-(2,6-dichlorophenyl)prop-2-en-1-one 1-(4-bromophenyl)-3-(4-chlorophenyl)prop-2-en-1-one 1-(2-chlorophenyl)-3-(2,6-dichlorophenyl)prop-2-en-1-one 1-(4-chlorophenyl)-3-(2,6-dichlorophenyl)prop-2-en-1-one 3-(2,6-dichlorophenyl)-1-(4-methoxyphenyl)prop-2-en-1-one 3-(4-chloro-1-methyl-1H-pyrazol-3-yl)-1-[4-(trifluoromethyl)phenyl]prop-2-en-1-one 3-(2,4-dichlorophenyl)-1-(2-methylphenyl)prop-2-en-1-one 3-(2,6-dichlorophenyl)-1-(2-methylphenyl)prop-2-en-1-one 3-(3,4-dichlorophenyl)-1-(2-methylphenyl)prop-2-en-1-one 3-(5-bromo-2-hydroxyphenyl)-1-(3-methylphenyl)prop-2-en-1-one 3-(5-bromo-2-hydroxyphenyl)-1-(4-methylphenyl)prop-2-en-1-one 3-(2,4-dichlorophenyl)-1-(3-methylphenyl)prop-2-en-1-one 3-(2,4-dichlorophenyl)-1-(4-methoxyphenyl)prop-2-en-1-one 1-[4-amino-2-(methylthio)-1,3-thiazol-5-yl]-3-(4-chlorophenyl)prop-2-en-1-one 1-(4-chlorophenyl)-3-[4-(trifluoromethyl)phenyl]prop-2-en-1-one 1-benzo[b]thiophen-3-yl-3-(4-chlorophenyl)prop-2-en-1-one 1,3-di(5-nitro-3-thienyl)prop-2-en-1-one 1-(4-bromophenyl)-3-(3,5-difluorophenyl)prop-2-en-1-one 3-(3,5-difluorophenyl)-1-(3-nitrophenyl)prop-2-en-1-one.

3. The method of claim 1 or 2 where said compound is an HGF/SF agonist or an HGF/SF antagonist.

4. The method of claim 1 wherein the modulating activity comprises promoting the proliferation of cells, including endothelial cells, vascular cells, hepatic cells, or renal cells, among others;

promoting angiogenesis;

promoting vascularization;

improving wound healing;

improving vascularization of wounds;

improving endothelial cell dysfunction;

improving blood flow to ischemic tissues; or other desirable activities attendant to the desirable biological activities of endogenously present or endogenously administered HGF/SF.

5. The method of claim 2 wherein the modulating activity comprises inhibiting angiogenesis or neovascularization;

prevention of tumor growth or metastasis;

inhibiting of scatter; or inhibiting anti-apoptotic activities.

* * * * *